(12) United States Patent  (10) Patent No.: US 7,208,502 B2
Solow-Cordero et al.  (45) Date of Patent: Apr. 24, 2007

(54) METHODS OF TREATING CONDITIONS ASSOCIATED WITH AN EDG-3 RECEPTOR

(75) Inventors: David Solow-Cordero, San Francisco, CA (US); Geetha Shankar, Palo Alto, CA (US); Juliet V. Spencer, San Mateo, CA (US); Charles Gluchowski, Danville, CA (US)

(73) Assignee: Maniv Energy Capital, Hasbrouck, NJ (US)

( * ) Notice: Subject to any disclaimer, the term of this patent is extended or adjusted under 35 U.S.C. 154(b) by 235 days.

(21) Appl. No.: 10/390,426

(22) Filed: Mar. 14, 2003

(65) Prior Publication Data

US 2007/0032459 A1 Feb. 8, 2007

Related U.S. Application Data

(63) Continuation-in-part of application No. 10/347,421, filed on Jan. 17, 2003, now abandoned.

(60) Provisional application No. 60/350,447, filed on Jan. 18, 2002.

(51) Int. Cl.
*A61K 31/47* (2006.01)
(52) U.S. Cl. .................................. 514/311
(58) Field of Classification Search ............... None
See application file for complete search history.

(56) References Cited

U.S. PATENT DOCUMENTS 3,178,348 A * 4/1965 Bickerton .................... 514/312
5,478,832 A * 12/1995 Inoue et al. ............ 514/263.22
5,622,967 A * 4/1997 Dolle et al. .................. 514/312
5,872,130 A * 2/1999 Fujikawa et al. ............ 514/311
6,077,851 A * 6/2000 Bjork et al. .................. 514/312

OTHER PUBLICATIONS

Harrison's Principles of Internal Medicine, vol. 1, 13th ed., Isselbacher et al. (eds.), published 1994 by McGraw-Hill, Inc., pp. 1108-1116.*
Cecil Text Book of Medicine, 21st ed., vol. 1, pp. 258-273 (2000).*
K. Bandoh et al., "Lysophosphatidic acid (LPA) receptors of the EDG family are differentially activated by LPA species Structure-activity relationship of cloned LPA receptors," *Federation of European Biochemical Societies*, 478 (2000) 159-165.
D. Im et al., "Molecular Cloning and Characterization of a Lysophosphatidic Acid Receptor, Edg-7, Expressed in Prostate," *The American Society for Pharmacology and Experimental Therapeutics*, 57:753-759 (2000).
Annals of the New York Academy of Sciences, vol. 905:1-357, Lysophospholipids and Eicosanoids in Biology and Pathophysiology, Edited by Edward J. Goetzl and Kevin R. Lynch, 2000.
M. Gräler et al., "EDG6, a Novel G-Protein-Coupled Receptor Related to Receptors for Bioactive Lysophospholipids, Is Specifically Expressed in Lymphoid Tissue," *Genomics* 53, 164-169 (1998), Article No. GE985491.

* cited by examiner

*Primary Examiner*—Raymond J. Henley, III
(74) *Attorney, Agent, or Firm*—Morgan, Lewis & Bockius, LLP

(57) ABSTRACT

In one aspect, the present invention provides a method of modulating an Edg-3 receptor mediated biological activity in a cell. A cell expressing the Edg-3 receptor is contacted with a modulator of the Edg-3 receptor sufficient to modulate the Edg-3 receptor mediated biological activity. In another aspect, the present invention provides a method for modulating an Edg-3 receptor mediated biological activity in a subject. A therapeutically effective amount of a modulator of the Edg-3 receptor is administered to the subject. In yet another aspect, compounds and composition useful for modulation of the Edg-3 receptor are presented.

34 Claims, 3 Drawing Sheets

% Inhibition of 101

Edg 3 $IC_{50}$ = 5.07 uM

Table 1

Selectivity of 101 for Edg-3

Figure 1:
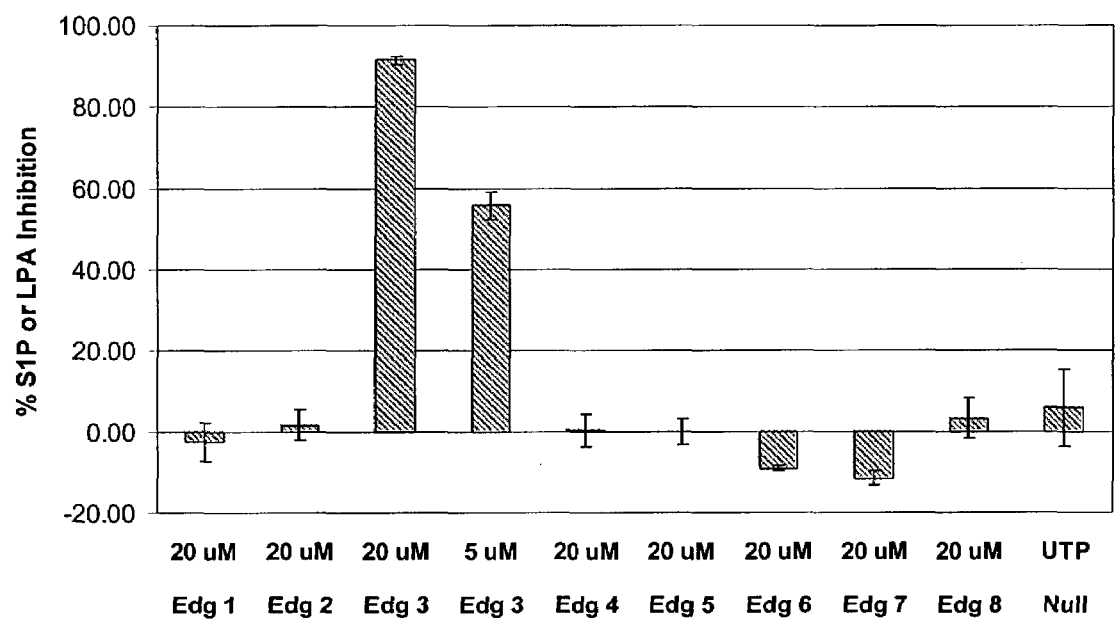

| | 101 |
|---|---|
| Edg 1 IC$_{50}$ μM | >20 |
| Edg 2 IC$_{50}$ μM | >20 |
| Edg 3 IC$_{50}$ μM | 5.07 |
| Edg 4 IC$_{50}$ μM | >20 |
| Edg 5 IC$_{50}$ μM | >20 |
| Edg 6 IC$_{50}$ μM | >20 |
| Edg 7 IC$_{50}$ μM | >20 |
| Edg 8 IC$_{50}$ μM | >20 |
| Fold Selectivity | >3.9 |

Table 2

Pharmacology Profiling of 301

| Adrenergic | |
|---|---|
| | Alpha 1, non-selective |
| | Alpha 2, non-selective |
| | Beta, non-selective |
| I. | Calcium Channels |
| | Type L, DHP |
| II. | Dopamine |
| | D2L |
| III. | Endothelin |
| | ETA |
| IV. | H1 central |
| V. | Muscarinic, non-selective, central |
| VI. | Serotonin |
| | 5HT1 non-selective |
| VII. | Angiotensin AT2 |

METHODS OF TREATING CONDITIONS ASSOCIATED WITH AN EDG-3 RECEPTOR

This is a continuation-in-part of U.S. patent application Ser. No. 10/347,421, filed Jan. 17, 2003, now abandoned which is entitled to and claims priority to U.S. Provisional Application Ser. No. 60/350,447, filed Jan. 18, 2002, each of which is incorporated herein by reference in its entirety.

1. FIELD OF INVENTION

The present invention relates generally to methods of modulating biological activity mediated by the Edg-3 receptor. More specifically, the present invention provides compounds and compositions, which may be used to selectively modulate, e.g., agonize or antagonize, the Edg-3 receptor. The present invention also provides methods for making these compounds.

2. BACKGROUND OF THE INVENTION

Recent studies have revealed a complex biological role for cell membrane phospholipids, which were previously believed to have only a structural function. Following cell activation, membrane phospholipids may be metabolized to eicosanoids and lysophospholipids, which are important regulators of cellular function and behavior. Lysophospholipids include compounds such as lysophosphatidic acid ("LPA"), sphingosine-1-phosphate ("S1P"), lysophosphatidylcholine and sphingosylphosphorylcholine and are important second messengers that can activate particular cell surface transmembrane G-protein coupled receptors known as endothelial gene differentiation ("Edg") receptors.

Two quite distinct subfamilies of GPCRs bind LPA and S1P specifically and transduce diverse cellular signals by associating with one or more G proteins. Based on amino acid sequence identities, S1P1 (Edg 1), S1P3 (Edg 3), S1P2 (Edg 5), and S1P5 (Edg 8) belong to one structural cluster and LPA1 (Edg 2), LPA2 (Edg 4) and LPA3 (Edg 7) are members of a second structural cluster (Goetzl, E. J., and Lynch, K. R. 2000, *Ann. N.Y. Acad. Sci.* 905:1–357). Members of both subfamilies range in size from 351 to 400 amino acids, and are encoded by chromosomes 1, 9 or 19. The amino acid sequence of S1P4 (Edg 6) lies between those of the two major clusters by amino acid sequence identity (Graler et al., 1998, *Genomics* 53:164–169). Edg-6, a novel G-protein-coupled receptor related to receptors for bioactive lysophospholipids, is specifically expressed in lymphoid tissue (Graler et al., 1998, *Genomics* 53:164–169). Currently, there are three known Edg receptors specifically activated by LPA (LPA1 or Edg 2, LPA2 or Edg 4 and LPA3 or Edg 7) and five known S1P receptors specifically activated by S1P (S1P1 or Edg 1, S1P2 or Edg 5, S1P3 or Edg 3, S1P4 or Edg 6, and S1P5 or Edg 8).

Edg-1 (human Edg-1, GenBank Accession No. AF233365), Edg-3 (human Edg-3, GenBank Accession No. X83864), Edg-5 (human Edg-5, GenBank Accession No. AF034780), Edg-6 (human Edg-6, GenBank Accession No. AJ000479) and Edg-8 (human Edg-8, GenBank Accession No. AF317676) receptors are activated by S1P, while LPA activates Edg-2 (human Edg-2, GenBank Accession No., U78192), Edg-4 (human Edg-4, GenBank Accession Nos. AF233092 or AF011466) and Edg-7 (human Edg-7, GenBank Accession No. AF127138) receptors. Although, all three LPA receptors (i.e., Edg-2, Edg-4 and Edg-7) bind LPA, compounds, which discriminate between these receptors have been identified (Im et al., 2000, *Mol. Pharmacol.* 57 (4):753–759). Further, Edg 2, Edg-4 and Edg-7 appear to exhibit significant pharmacological differences (Bandoh et al., 2000, *FEBS Lett.* 478:159–165).

Importantly, Edg receptors are believed to mediate critical cellular events such as cell proliferation and cell migration, which makes these receptors attractive therapeutic targets. However, currently known compounds, which bind to LPA, are almost exclusively phospholipids (e.g., LPA and S1P, analogs of LPA and S1P, dioctyl glycerol, etc). Most of these phospholipids compounds fail to effectively discriminate between different Edg receptors and have poor physicochemical properties, which limits their potential use as pharmaceutical agents. Thus, there exists a need for compounds, which are not phospholipids that bind or otherwise regulate Edg receptors and can also selectively bind to a specific Edg receptor.

3. SUMMARY OF THE INVENTION

The present invention addresses these and other needs by providing compounds that modulate the S1P3 or Edg-3 receptor (e.g. human Edg-3, GenBank Accession No. X83864). Such compounds preferably selectively bind or otherwise modulate the Edg-3 receptor.

In one aspect, the present invention provides methods for modulating Edg-3 receptor mediated biological activity. The present invention also provides methods for using Edg-3 modulators (i.e., agonists or antagonists) in treating or preventing diseases such as ovarian cancer, peritoneal cancer, endometrial cancer, cervical cancer, breast cancer, colorectal cancer, uterine cancer, stomach cancer, small intestine cancer, thyroid cancer, lung cancer, kidney cancer, pancreas cancer and prostrate cancer; acute lung diseases, adult respiratory distress syndrome ("ARDS"), acute inflammatory exacerbation of chronic lung diseases such as asthma, surface epithelial cell injury, (e.g., transcorneal freezing or cutaneous burns) and cardiovascular diseases (e.g., ischemia) in a subject in need of such treatment or prevention.

In a another aspect, the present invention provides methods for using Edg-3 modulators (i.e., agonists or antagonists) in treating or preventing disorders such as, but not limited to, vasoconstriction in cerebral arteries, autoimmune and related immune disorders, including, but not limited to, systemic lupus erythematosus (SLE), rheumatoid arthritis, non-glomerular nephrosis, psoriasis, chronic active hepatitis, ulcerative colitis, Crohn's disease, Behçet's disease, chronic glomerulonephritis, chronic thrombocytopenic purpura, and autoimmune hemolytic anemia. Additionally, Edg-3 antagonists can also be used in organ transplantation. In yet another embodiment, Edg-3 agonists and antagonists can be used to treat vascular occlusive disorders. For example, activation of Edg-3 receptors by using an Edg-3 agonist will result in increased vasoconstriction which is beneficial in conditions such as migraine headaches. Inhibition of Edg-3 by an Edg3 antagonist will be beneficial in conditions such as a stroke, a subarachnoid hemorrhage, or a vasospasm such as a cerebral vasospasm. (PCT WO 01/69252 A1).

In still other aspects, the present invention provides a method of modulating an Edg-3 receptor mediated biological activity in a cell. A cell expressing the Edg-3 receptor is contacted with an amount of an Edg-3 receptor modulator sufficient to modulate the Edg-3 receptor mediated biological activity.

In yet other aspects, the present invention provides a method for modulating an Edg-3 receptor mediated biological activity in a subject. In such a method, an amount of a modulator of the Edg-3 receptor effective to modulate an Edg-3 receptor mediated biological activity is administered to the subject.

The present invention also provides compounds and compositions for use in modulating (i.e., agonizing or antagonizing) Edg-3 receptor mediated biological activity or treating or preventing diseases such as those mentioned above as well as methods for synthesizing the compounds.

In certain embodiments, The Edg-3 receptor modulators are compounds of structural formula (I):

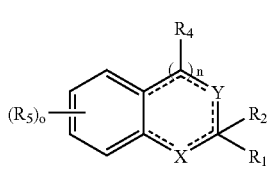

(I)

or a pharmaceutically available solvate or hydrate thereof, wherein:

n=0 or 1;

o is 0, 1, 2, 3 or 4;

X is C, $NR_7$ O or S;

Y is C, $NR_8$ O or S;

$R_1$ is either absent or hydrogen, alkyl, substituted alkyl, acyl, substituted acyl, acylamino, substituted acylamino, alkylamino, substituted alkylamino, alkylthio, substituted alkylthio, alkoxy, substituted alkoxy, alkoxycarbonyl, substituted alkoxycarbonyl, alkylarylamino, substituted alkylarylamino, arylalkyloxy, substituted arylalkyloxy, amino, aryl, substituted aryl, arylalkyl, substituted arylalkyl, arylamino, substituted arylamino, arylsulfonyl, substituted arylsulfonyl, carboxy, carbamoyl, substituted carbamoyl, cycloalkyl, substituted cycloalkyl, cycloheteroalkyl, substituted cycloheteroalkyl, dialkylamino, substituted dialkylamino, heteroaryloxy, substituted heteroaryloxy, heteroaryl, substituted heteroaryl, heteroalkyl, or substituted heteroalkyl;

$R_2$, $R_3$ and $R_4$ are independently hydrogen, alkyl, substituted alkyl, acyl, substituted acyl, acylamino, substituted acylamino, alkylamino, substituted alkylamino, alkylthio, substituted alkylthio, alkoxy, substituted alkoxy, alkoxycarbonyl, substituted alkoxycarbonyl, alkylarylamino, substituted alkylarylamino, arylalkyloxy, substituted arylalkyloxy, amino, aryl, substituted aryl, arylalkyl, substituted arylalkyl, arylamino, substituted arylamino, arylsulfonyl, substituted arylsulfonyl, carboxy, carbamoyl, substituted carbamoyl, cycloalkyl, substituted cycloalkyl, cycloheteroalkyl, substituted cycloheteroalkyl, dialkylamino, substituted dialkylamino, heteroaryloxy, substituted heteroaryloxy, heteroaryl, substituted heteroaryl, heteroalkyl, or substituted heteroalkyl;

each $R_5$ is independently, alkyl, substituted alkyl, acyl, substituted acyl, acylamino, substituted acylamino, alkylamino, substituted alkylamino, alkylthio, substituted alkylthio, alkoxy, substituted alkoxy, alkoxycarbonyl, substituted alkoxycarbonyl, alkylarylamino, substituted alkylarylamino, arylalkyloxy, substituted arylalkyloxy, amino, aryl, substituted aryl, arylalkyl, substituted arylalkyl, arylsulfonyl, substituted arylsulfonyl, azido, carboxy, carbamoyl, substituted carbamoyl, carboxyl, cyano, cycloalkyl, substituted cycloalkyl, cycloheteroalkyl, substituted cycloheteroalkyl, dialkylamino, substituted dialkylamino, halo, heteroaryloxy, substituted heteroaryloxy, heteroaryl, substituted heteroaryl, heteroalkyl, substituted heteroalkyl, hydroxyl, nitro or thio; and $R_7$ and $R_8$ are independently absent, hydrogen, alkyl, substituted alkyl, acyl or substituted acyl.

In other embodiments, Edg-3 receptor modulators are compounds of structural formula (II):

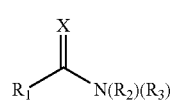

(II)

or a pharmaceutically available solvate or hydrate thereof, wherein; each of $R_1$, $R_2$ and $R_3$ is independently —H, -halo, —$NO_2$, —CN, —$C(R_5)_3$, —$(CH_2)_m OH$, —$N(R_5)(R_5)$, —$O(CH_2)_m R_5$, —$C(O)R_5$, —$C(O)NR_5 R_5$, —$C(O)NH(CH_2)_m(R_5)$, —$OCF_3$, -benzyl, —$CO_2 CH(R_5)(R_5)$, —$(C_1$–$C_{10})$alkyl, —$(C_2$–$C_{10})$alkenyl, —$(C_2$–$C_{10})$alkynyl, —$(C_3$–$C_{10})$cycloalkyl, —$(C_8$–$C_{14})$bicycloalkyl, —$(C_5$–$C_{10})$cycloalkenyl, —$(C_5)$heteroaryl, —$(C_6)$heteroaryl, —$(C_5$–$C_{10})$heteroaryl, -naphthyl, —$(C_3$–$C_{10})$heterocycle, —$CO_2(CH_2)_m R_5$, —N(OH)aryl, —NHC(O)$R_5$, —NHC(O)OR$_5$, —NHC(O)NHR$_5$, -heterocylcoalkyl, —$(C_1$–$C_{10})$alkylNHC(O)(CH$_2)_m R_5$, —$(C_1$–$C_{10})$alkylNR$_5 R_5$, —OC(O)(CH$_2)_m CHR_5 R_5$, —CO$_2$(CH$_2)_m$CHR$_5 R_5$, —OC(O)OR$_5$, —SR$_5$, —S(O)R$_5$, —S(O)$_2 R_5$, —S(O)$_2$NHR$_5$, or

$R_3$ is —H —$C(R_5)_3$, —$(CH_2)_m OH$, —$C(O)R_5$, —$C(O)NR_5 R_5$, —$C(O)NH(CH_2)_m(R_5)$, -benzyl, —$CO_2 CH(R_5)(R_5)$, —$(C_1$–$C_{10})$alkyl, —$(C_2$–$C_{10})$alkenyl, —$(C_2$–$C_{10})$alkynyl, —$(C_3$–$C_{10})$cycloalkyl, —$(C_8$–$C_{14})$bicycloalkyl, —$(C_5$–$C_{10})$cycloalkenyl, —$(C_5)$heteroaryl, —$(C_6)$heteroaryl, —$(C_5$–$C_{10})$heteroaryl, -naphthyl, —$(C_3$–$C_{10})$heterocycle, —$CO_2(CH_2)_n R_5$, —N(OH)aryl, —NHC(O)$R_5$, —NHC(O)OR$_5$, —NHC(O)NHR$_5$, —N=C(aryl), -heterocylcoalkyl, —$(C_1$–$C_{10})$alkylNHC(O)(CH$_2)_m R_5$, —$(C_1$–$C_{10})$alkylNR$_5 R_5$, —OC(O)(CH$_2)_m CHR_5 R_5$, —CO$_2$(CH$_2)_m$CHR$_5 R_5$, —OC(O)OR$_5$, —SR$_5$, —S(O)R$_5$, —S(O)$_2 R_5$, —S(O)$_2$NHR$_5$, or

wherein; each $R_5$ and $R_6$ is independently —H, -halo, —$NO_2$, —CN, —OH, —$CO_2 H$, —N($C_1$–$C_{10}$)alkyl ($C_1$–$C_{10}$)alkyl, —O($C_1$–$C_{10}$)alkyl, —C(O)($C_1$–$C_{10}$)alkyl, —C(O)NH(CH$_2)_m$($C_1$–$C_{10}$)alkyl, —OCF$_3$, -benzyl, —CO$_2$(CH$_2)_m$CH(($C_1$–$C_{10}$)alkyl($C_1$–$C_{10}$)alkyl), —CO$_2$($C_1$–$C_{10}$)alkyl, —($C_1$–$C_{10}$)alkyl, —($C_2$–$C_{10}$)alkenyl, —($C_2$–$C_{10}$)alkynyl, —($C_3$–$C_{10}$)cycloalkyl, —($C_8$–$C_{14}$)bicycloalkyl, —($C_5$–$C_{10}$)cycloalkenyl, —($C_5$)heteroaryl, —($C_6$)heteroaryl, -phenyl, naphthyl, —($C_3$–$C_{10}$)heterocycle, —$CO_2$($CH_2$)$_m$($C_1$–$C_{10}$)alkyl, —$CO_2$($CH_2$)$_m$H, —NHC(O)($C_1$–$C_{10}$)alkyl, —NHC(O)NH($C_1$–$C_{10}$)alkyl, —NH(aryl), —N=C(aryl), —OC(O)O($C_1$–$C_{10}$)alkyl, or —$SO_2NH_2$;

X is O, S, C($R_5$)($R_5$) or N($R_5$);

$R_1$, $R_2$ or $R_3$ taken in combination can form one or more substituted or unsubstituted 5 or 6 membered cyclic or heterocyclic rings or a 6-membered aromatic ring;

each m is independently an integer ranging from 0 to 8; and each p is independently an integer ranging from 0 to 5.

In yet other embodiments, Edg-3 receptor modulators are compounds of structural formula (III):

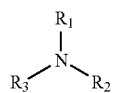

(III)

or a pharmaceutically available solvate or hydrate thereof, wherein; each of $R_1$, $R_2$ and $R_3$ is independently —H, -halo, —$NO_2$, —CN, —C($R_5$)$_3$, —($CH_2$)$_m$OH, —N($R_5$)($R_5$), —O($CH_2$)$_m$$R_5$, —C(O)$R_5$, —C(O)N$R_5$$R_5$, —C(O)NH($CH_2$)$_m$($R_5$), —$OCF_3$, -benzyl, —$CO_2$CH($R_5$)($R_5$), —($C_1$–$C_{10}$)alkyl, —($C_2$–$C_{10}$)alkenyl, —($C_2$–$C_{10}$)alkynyl, —($C_3$–$C_{10}$)cycloalkyl, —($C_8$–$C_{14}$)bicycloalkyl, —($C_5$–$C_{10}$)cycloalkenyl, —($C_5$)heteroaryl, —($C_6$)heteroaryl, —($C_5$–$C_{10}$)heteroaryl, -naphthyl, —($C_3$–$C_{10}$)heterocycle, —$CO_2$($CH_2$)$_m$$R_5$, —N(OH)aryl, —NHC(O)$R_5$, —NHC(O)O$R_5$, —NHC(O)NH$R_5$, -heterocylcoalkyl, —C(S)N($R_5$)($R_5$), —($C_1$–$C_{10}$)alkylNHC(O)($CH_2$)$_m$$R_5$, —($C_1$–$C_{10}$)alkylN$R_5$$R_5$, —OC(O)($CH_2$)$_m$CH$R_5$$R_5$, —$CO_2$($CH_2$)$_m$CH$R_5$$R_5$, —OC(O)O$R_5$, —S$R_5$, —S(O)$R_5$, —S(O)$_2$$R_5$, —S(O)$_2$NH$R_5$, or

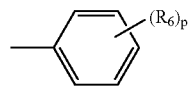

$R_3$ is —H —C($R_5$)$_3$, —($CH_2$)$_m$OH, —C(O)$R_5$, —C(O)N$R_5$$R_5$, —C(O)NH($CH_2$)$_m$($R_5$), -benzyl, —$CO_2$CH($R_5$)($R_5$), —($C_1$–$C_{10}$)alkyl, —($C_2$–$C_{10}$)alkenyl, —($C_2$–$C_{10}$)alkynyl, —($C_3$–$C_{10}$)cycloalkyl, —($C_8$–$C_{14}$)bicycloalkyl, —($C_5$–$C_{10}$)cycloalkenyl, —($C_5$)heteroaryl, —($C_6$)heteroaryl, —($C_5$–$C_{10}$)heteroaryl, -naphthyl, —($C_3$–$C_{10}$)heterocycle, —$CO_2$($CH_2$)$_m$$R_5$, —N(OH)aryl, —NHC(O)$R_5$, —NHC(O)O$R_5$, —NHC(O)NH$R_5$, —N=C(aryl), -heterocylcoalkyl, —($C_1$–$C_{10}$)alkylNHC(O)($CH_2$)$_m$$R_5$, —($C_1$–$C_{10}$)alkylN$R_5$$R_5$, —OC(O)($CH_2$)$_n$CH$R_5$$R_5$, —$CO_2$($CH_2$)$_n$CH$R_5$$R_5$, —OC(O)O$R_5$, —S$R_5$, —S(O)$R_5$, —S(O)$_2$$R_5$, —S(O)$_2$NH$R_5$, or

wherein;

each $R_5$ and $R_6$ is independently —H, -halo, —$NO_2$, —CN, —OH, —$CO_2$H, —N($C_1$–$C_{10}$)alkyl($C_1$–$C_{10}$)alkyl, —O($C_1$–$C_{10}$)alkyl, —C(O)($C_1$–$C_{10}$)alkyl, —C(O)NH($CH_2$)$_m$ ($C_1$–$C_{10}$)alkyl, —$OCF_3$, -benzyl, —$CO_2$($CH_2$)$_m$CH(($C_1$–$C_{10}$)alkyl($C_1$–$C_{10}$)alkyl), —$CO_2$($C_1$–$C_{10}$)alkyl, —($C_1$–$C_{10}$)alkyl, —($C_2$–$C_{10}$)alkenyl, —($C_2$–$C_{10}$)alkynyl, —($C_3$–$C_{10}$)cycloalkyl, —($C_8$–$C_4$)bicycloalkyl, —($C_5$–$C_{10}$)cycloalkenyl, —($C_5$)heteroaryl, —($C_6$)heteroaryl, -phenyl, naphthyl, —($C_3$–$C_{10}$)heterocycle, —$CO_2$($CH_2$)$_m$($C_1$–$C_{10}$)alkyl, —$CO_2$($CH_2$)$_m$H, —NHC(O)($C_1$–$C_{10}$)alkyl, —NHC(O)NH($C_1$–$C_{10}$)alkyl, —NH(aryl), —N=C(aryl), —OC(O)O($C_1$–$C_{10}$)alkyl, or —$SO_2NH_2$;

X is O, S, or N($R_5$);

$R_1$, $R_2$ or $R_3$ taken in combination can form one or more substituted or unsubstituted 5 or 6 membered cyclic or heterocyclic rings or a 6-membered aromatic ring;

two $R_6$ groups on adjacent carbon atoms can together form a 5 or 6 membered cyclic or heterocyclic ring or a 6-membered aromatic ring;

each m is independently an integer ranging from 0 to 8; and each p is independently an integer ranging from 0 to 5.

4. BRIEF DESCRIPTION OF THE FIGURES

FIG. 1 illustrates the selectivity of 101 for the Edg-3 receptor;

Table 1 also illustrates the selectivity of 101 for the Edg-3 receptor; and

Table 2 presents the pharmacological profile of compound 101.

5. DETAILED DESCRIPTION OF THE INVENTION

5.1. Definitions

"Compounds of the invention" refers generally to any modulator of the S1P3 or Edg-3 receptor (e.g., human Edg-3, GenBank Accession No. X83864) and includes any Edg-3 receptor modulator encompassed by generic formulae disclosed herein and further includes any specific Edg-3 receptor modulator within those formulae whose structure is disclosed herein. The compounds of the invention may be identified either by their chemical structure and/or chemical name. If the chemical structure and chemical name conflict, the chemical structure is determinative of the identity of the compound. The compounds of the invention may contain one or more chiral centers and/or double bonds and therefore, may exist as stereoisomers, such as double-bond isomers (i.e., geometric isomers), enantiomers or diastereomers. Accordingly, the chemical structures depicted herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds of the invention may also exist in several tautomeric forms including, but not limited to, the enol form, the keto form and mixtures thereof. Accordingly, the chemical structures depicted herein encompass all possible tautomeric forms of the illustrated compounds. The compounds of the invention also include isotopically labeled compounds where one or more atoms have an atomic mass different from the atomic mass conventionally found in nature.

Examples of isotopes that may be incorporated in the compounds of the invention include, but are not limited to, $^2$H, $^3$H, $^{13}$C, $^{14}$C, $^{15}$N, $^{18}$O, $^{17}$O, $^{31}$P, $^{32}$P, $^{35}$S, $^{18}$F and $^{36}$Cl. Further, it should be understood that when partial structures of the compounds of the invention are illustrated, brackets indicate the point of attachment of the partial structure to the rest of the compound.

"Composition of the invention" refers to at least one compound of the invention and a pharmaceutically acceptable vehicle, with which the compound is administered to a patient. When administered to a patient, the compounds of the invention are administered in isolated form, which means separated from a synthetic organic reaction mixture.

"Alkyl" refers to a saturated or unsaturated, branched, straight-chain or cyclic monovalent hydrocarbon group derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-prop an-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like.

The term "alkyl" is specifically intended to include groups having any degree or level of saturation, i.e., groups having exclusively single carbon—carbon bonds, groups having one or more double carbon—carbon bonds, groups having one or more triple carbon—carbon bonds and groups having mixtures of single, double and triple carbon—carbon bonds. Where a specific level of saturation is intended, the expressions "alkanyl," "alkenyl," and "alkynyl" are used. Preferably, an alkyl group comprises from 1 to 20 carbon atoms.

"Alkanyl" refers to a saturated branched, straight-chain or cyclic alkyl group derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkenyl" refers to an unsaturated branched, straight-chain or cyclic alkyl group having at least one carbon—carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl" refers to an unsaturated branched, straight-chain or cyclic alkyl group having at least one carbon—carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Acyl" refers to a radical —C(O)R, where R is hydrogen, alkyl, cycloalkyl, cycloheteroalkyl, aryl, arylalkyl, heteroalkyl, heteroaryl, heteroarylalkyl as defined herein. Representative examples include, but are not limited to formyl, acetyl, cylcohexylcarbonyl, cyclohexylmethylcarbonyl, benzoyl, benzylcarbonyl and the like.

"Acylamino" refers to a radical —NR'C(O)R, where R' is hydrogen, alkyl, cycloalkyl, cycloheteroalkyl, aryl, arylalkyl, heteroalkyl, heteroaryl, heteroarylalkyl and R is hydrogen, alkyl, alkoxy, cycloalkyl, cycloheteroalkyl, aryl, arylalkyl, heteroalkyl, heteroaryl or heteroarylalkyl, as defined herein. Representative examples include, but are not limited to, formylamino, acetylamino, cylcohexylcarbonylamino, cyclohexylmethyl-carbonylamino, benzoylamino, benzylcarbonylamino and the like.

"Alkylamino" refers to a radical —NHR where R represents an alkyl or cycloalkyl group as defined herein. Representative examples include, but are not limited to, methylamino, ethylamino, 1-methylethylamino, cyclohexyl amino and the like.

"Alkoxy" refers to a radical —OR where R represents an alkyl or cycloalkyl group as defined herein. Representative examples include, but are not limited to, methoxy, ethoxy, propoxy, butoxy, cyclohexyloxy and the like.

"Alkoxyamino" refers to a radical —N(H)OR where R represents an alkyl or cycloalkyl group as defined herein.

"Alkoxycarbonyl" refers to a radical —C(O)-alkoxy where alkoxy is as defined herein.

"Alkylarylamino" refers to a radical —NRR' where R represents an alkyl or cycloalkyl group and R' is an aryl as defined herein "Alkylsulfonyl" refers to a radical —S(O)$_2$R where R is an alkyl or cycloalkyl group as defined herein. Representative examples include, but are not limited to methylsulfonyl, ethylsulfonyl, propylsulfonyl, butylsulfonyl and the like.

"Alkylsulfinyl" refers to a radical —S(O)R where R is an alkyl or cycloalkyl group as defined herein. Representative examples include, but are not limited to, methylsulfinyl, ethylsulfinyl, propylsulfinyl, butylsulfinyl and the like.

"Alkylthio" refers to a radical —SR where R is an alkyl or cycloalkyl group as defined herein that may be optionally substituted as defined herein. Representative examples include, but are not limited to methylthio, ethylthio, propylthio, butylthio, and the like.

"Amino" refers to the radical —NH$_2$.

"Aryl" refers to a monovalent aromatic hydrocarbon group derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. Preferably, an aryl group comprises from 6 to 20 carbon atoms.

"Arylalkyl" refers to an acyclic alkyl group in which one of the hydrogen atoms bonded to a carbon atom, typically a terminal or sp$^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. Preferably, an arylalkyl group is ($C_6$–$C_{30}$) arylalkyl, e.g., the alkanyl, alkenyl or alkynyl moiety of the arylalkyl group is ($C_1$–$C_{10}$) and the aryl moiety is ($C_6$–$C_{20}$).

"Arylalkyloxy" refers to an —O-arylalkyl radical where arylalkyl is as defined herein.

"Arylamino" means a radical —NHR where R represents an aryl group as defined herein.

"Aryloxycarbonyl" refers to a radical —C(O)—O-aryl where aryl is as defined herein.

"Arylsulfonyl" refers to a radical —S(O)$_2$R where R is an aryl or heteroaryl group as defined herein.

"Azido" refers to the radical —N$_3$.

"Carbamoyl" refers to the radical —C(O)N(R)$_2$ where each R group is independently hydrogen, alkyl, cycloalkyl or aryl as defined herein, which may be optionally substituted as defined herein.

"Carboxy" refers to the radical —C(O)OH.

"Carboxyamino" refers to the radical —N(H)C(O)OH.

"Cyanato" refers to the radical —OCN.

"Cyano" refers to the radical —CN.

"Cycloalkyl" refers to a saturated or unsaturated cyclic alkyl group. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane, and the like. In a preferred embodiment, the cycloalkyl group is ($C_3$–$C_{10}$) cycloalkyl, more preferably ($C_3$–$C_6$) cycloalkyl.

"Cycloheteroalkyl" refers to a saturated or unsaturated cyclic alkyl group in which one or more carbon atoms (and any associated hydrogen atoms) are independently replaced with the same or different heteroatom. Typical heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from dioxanes, dioxolanes, epoxides, imidazolidine, morpholine, piperazine, piperidine, pyrazolidine, pyrrolidine, quinuclidine, tetrahydrofuran, tetrahydropyran and the like.

"Cycloheteroalkyloxycarbonyl" refers to a radical —C(O)—OR where R is cycloheteroalkyl is as defined herein.

"Dialkylamino" means a radical —NRR' where R and R' independently represent an alkyl, substituted alkyl, aryl, substituted aryl, cycloalkyl, substituted cycloalkyl, cycloheteroalkyl, substituted cycloheteroalkyl, heteroaryl, or substituted heteroaryl group as defined herein. Representative examples include, but are not limited to dimethylamino, methylethylamino, di-(1-methylethyl)amino, (cyclohexyl) (methyl)amino, (cyclohexyl)(ethyl)amino, (cyclohexyl) (propyl)amino, and the like.

"Halo" means fluoro, chloro, bromo, or iodo.

"Haloalkyl" means an alkyl radical substituted by one or more halo atoms wherein alkyl and halo is as defined herein.

"Heteroalkyloxy" means an —O-heteroalkyl group where heteroalkyl is as defined herein.

"Heteroalkyl, Heteroalkanyl, Heteroalkenyl, Heteroalkynyl" refer to alkyl, alkanyl, alkenyl and alkynyl groups, respectively, in which one or more of the carbon atoms (and any associated hydrogen atoms) are each independently replaced with the same or different heteroatomic groups. Typical heteroatomic groups include, but are not limited to, —O—, —S—, —O—O—, —S—S—, —O—S—, —NR', =N—N=, —N=N—, —N=N—NR'—, —PH—, —P(O)$_2$—, —O—P(O)$_2$—, —S(O)—, —S(O)$_2$—, —SnH$_2$— and the like, wherein R' is hydrogen, alkyl, substituted alkyl, cycloalkyl, substituted cycloalkyl, aryl or substituted aryl.

"Heteroaryl" refers to a monovalent heteroaromatic group derived by the removal of one hydrogen atom from a single atom of a parent heteroaromatic ring system. Typical heteroaryl groups include, but are not limited to, groups derived from acridine, arsindole, carbazole, carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Preferably, the heteroaryl group is between 5–20 membered heteroaryl, with 5–10 membered heteroaryl being particularly preferred. Preferred heteroaryl groups are those derived from thiophene, pyrrole, benzothiophene, benzofuran, indole, pyridine, quinoline, imidazole, oxazole and pyrazine.

"Heteroaryloxy" refers to an —O-heteroarylalkyl radical where heteroarylalkyl is as defined herein.

"Heteroaryloxycarbonyl" refers to a radical —C(O)—OR where R is heteroaryl as defined herein.

"Heteroarylalkyl" refers to an acyclic alkyl group in which one of the hydrogen atoms bonded to a carbon atom, typically a terminal or sp$^3$ carbon atom, is replaced with a heteroaryl group. Where specific alkyl moieties are intended, the nomenclature heteroarylalkanyl, heteroarylalkenyl and/or heterorylalkynyl is used. In preferred embodiments, the heteroarylalkyl group is a 6–30 membered heteroarylalkyl, e.g., the alkanyl, alkenyl or alkynyl moiety of the heteroarylalkyl is 1–10 membered and the heteroaryl moiety is a 5–20 membered heteroaryl.

"Hydroxy" refers to the radical —OH.

"Leaving group" has the meaning conventionally associated with it in synthetic organic chemistry, i.e., an atom or a group capable of being displaced by a nucleophile and includes halo (such as chloro, bromo, and iodo), alkoxycarbonyl (e.g., acetoxy), aryloxycarbonyl, mesyloxy, tosyloxy, trifluoromethanesulfonyloxy, aryloxy (e.g., 2,4-dinitrophenoxy), methoxy, N,O-dimethylhydroxylamino, and the like.

"Nitro" refers to the radical —NO$_2$.

"Oxo" refers to the divalent radical =O.

"Pharmaceutically acceptable" means approved by a regulatory agency of the Federal or a state government or listed in the U.S. Pharmacopoeia or other generally recognized pharmacopoeia for use in animals, and more particularly in humans.

"Pharmaceutically acceptable salt" refers to a salt of a compound of the invention that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo

[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like.

"Pharmaceutically acceptable vehicle" refers to a diluent, adjuvant, excipient or carrier with which a compound of the invention is administered.

"Patient" includes humans. The terms "human" and "patient" are used interchangeably herein.

"Preventing" or "prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease).

"Prodrug" refers to a pharmacologically inactive derivative of a drug molecule that requires a transformation within the body to release the active drug. Typically, prodrugs are designed to overcome pharmaceutical and/or pharmacokinetically based problems associated with the parent drug molecule that would otherwise limit the clinical usefulness of the drug.

"Promoiety" refers to a form of protecting group that when used to mask a functional group within a drug molecule converts the drug into a prodrug. Typically, the promoiety will be attached to the drug via bond(s) that are cleaved by enzymatic or non-enzymatic means in vivo. Ideally, the promoiety is rapidly cleared from the body upon cleavage from the prodrug.

"Protecting group" refers to a grouping of atoms that when attached to a reactive group in a molecule masks, reduces or prevents that reactivity. Examples of protecting groups can be found in Green et al., "Protective Groups in Organic Chemistry", (Wiley, $2^{nd}$ ed. 1991) and Harrison et al., "Compendium of Synthetic Organic Methods", Vols. 1–8 (John Wiley and Sons, 1971–1996). Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenyl-methyloxycarbonyl ("FMOC"), nitro-veratryloxycarbonyl ("NVOC") and the like. Representative hydroxy protecting groups include, but are not limited to, those where the hydroxy group is either acylated or alkylated such as benzyl, and trityl ethers as well as alkyl ethers, tetrahydropyranyl ethers, trialkylsilyl ethers and allyl ethers.

"Substituted" refers to a group in which one or more hydrogen atoms are each independently replaced with the same or different substituent(s). Typical substituents include, but are not limited to, —X, —$R_{14}$, —$O^-$, =O, —$OR_{14}$, —$SR_{14}$, —$S^-$, =S, —$NR_{14}R_{15}$, =$NR_{14}$, —$CX_3$, —$CF_3$, —CN, —OCN, —SCN, —NO, —$NO_2$, =$N_2$, —$N_3$, —$S(O)_2O^-$, —$S(O)_2OH$, —$S(O)_2R_{14}$, —$OS(O_2)O^-$, —$OS(O)_2R_{14}$, —$P(O)(O^-)_2$, —$P(O)(OR_{14})(O^-)$, —$OP(O)(OR_{14})(OR_{15})$, —$C(O)R_{14}$, —$C(S)R_{14}$, —$C(O)OR_{14}$, —$C(O)NR_{14}R_{15}$, —C(O)O—, —$C(S)OR_{14}$, —$NR_{16}C(O)NR_{14}R_{15}$, —$NR_{16}C(S)NR_{14}R_{15}$, —$NR_{17}C(NR_{16})NR_{14}R_{15}$ and —$C(NR_{16})NR_{14}R_{15}$, where each X is independently a halogen; each $R_{14}$, $R_{15}$, $R_{16}$ and $R_{17}$ are independently hydrogen, alkyl, substituted alkyl, aryl, substituted alkyl, arylalkyl, substituted alkyl, cycloalkyl, substituted alkyl, cycloheteroalkyl, substituted cycloheteroalkyl, heteroalkyl, substituted heteroalkyl, heteroaryl, substituted heteroaryl, heteroarylalkyl, substituted heteroarylalkyl, —$NR_{18}R_{19}$, —$C(O)R_{18}$ or —$S(O)_2R_{18}$ or optionally $R_{18}$ and $R_{19}$ together with the atom to which they are both attached form a cycloheteroalkyl or substituted cycloheteroalkyl ring; and $R_{18}$ and $R_{19}$ are independently hydrogen, alkyl, substituted alkyl, aryl, substituted alkyl, arylalkyl, substituted alkyl, cycloalkyl, substituted alkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Sulfonyl" refers to the divalent radical —$S(O_2)$—.

"Sulfonylamino" refers to a radical —NR'S($O_2$)R, where R' and R are each independently hydrogen, alkyl, cycloalkyl, cycloheteroalkyl, aryl, arylalkyl, heteroalkyl, heteroaryl, heteroarylalkyl, as defined herein.

"Therapeutically effective amount" means the amount of a compound that, when administered to a patient for treating a disease, is sufficient to effect such treatment for the disease. The "therapeutically effective amount" will vary depending on the compound, the disease and its severity and the age, weight, etc., of the patient to be treated.

"Thio" refers to the radical —SH.

"Thiocyanato" refers to the radical —SCN.

"Thiono" refers to the divalent radical =S.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder.

Reference will now be made in detail to preferred embodiments of the invention. While the invention will be described in conjunction with the preferred embodiments, it will be understood that it is not intended to limit the invention to those preferred embodiments. To the contrary, it is intended to cover alternatives, modifications, and equivalents as may be included within the spirit and scope of the invention as defined by the appended claims.

5.2. The Use of the Compounds of the Invention

The present invention provides a method of modulating an S1P3 or Edg-3 receptor (e.g., human Edg-3, GenBank Accession No. X83864) mediated biological activity. A cell expressing the Edg-3 receptor is contacted with an amount of an Edg-3 receptor agonist or antagonist sufficient to modulate an Edg-3 receptor mediated biological activity.

Those of skill in the art will appreciate that Edg-3 is a G protein coupled receptor ("GPCR"). The Edg-3 (S1P3) receptor is encoded by an endothelial differentiation gene and along with related receptors, Edg-1 (S1P1), Edg-5 (S1P2), Edg-6 (S1P4) and Edg-8 (S1P5), binds sphingosine-1-phosphate ("S1P"). Preferably, the Edg-3 receptor is a human receptor.

The Edg-3 receptor may be expressed by recombinant DNA methods well known to those of skill in the art. Particularly useful cell types for expressing and assaying Edg-3 include, but are not limited to, HTC4 (rat hepatoma cells), RH7777 (rat hepatoma cells), HepG2 (human hepatoma cells), CHO (Chinese hamster ovary cells) and HEK-293 (human embryonic kidney cells). Particularly useful vectors for expressing G-protein receptors include, but are not limited to, pLXSN and pCMV (Clontech Labs, Palo Alto, Calif.; Invitrogen Corporation, Carlsbad, Calif.).

DNA encoding Edg-3 is well known (e.g., human Edg-3, GenBank Accession No. X83864) and can be transfected into human or mammalian cells according to methods known to those of skill in the art. For example, DNA encoding human Edg-3 can be co-transfected with a standard packaging vector, such as those described above, which provides an ecotropic envelope for viral replication, into a packaging cell line such as GP-293 (Clontech Labs, Palo Alto, Calif.).

Alternatively, DNA encoding Edg-3 can be transfected into the EcoPack-293 cell line which has, in addition to gag and pol, the env gene to produce an ecotropic envelope. Both methods (i.e., co-transfection with a packaging vector or use of EcoPack-293) enable the production of an ecotropic envelope for viral packaging, and can thus advantageously be used to transfect rat and mouse cells. For use in human and other mammalian cells, AmphoPack-293 cell line can be used (Clontech, Palo Alto, Calif.).

A number of natural cell lines naturally express Edg-3 receptors. These include, but are not limited to, CaOV-3 human ovarian cancer cells, MDA-MB-453 and MDA-MB-231 breast cancer cells, HT-1080 human fibrosarcoma, HUVEC cells, OV202 human ovarian cancer cells, Hela human cervical adenocarcinoam cells, HEK293 human embryonic kidney cells, NIH 3T3 mouse fibroblast cells (ATCC, Manassas, Va.; Vec Technologies Inc., Rensselaer, N.Y.; Dr. Edward Goetzl, University of California, San Francisco, San Francisco, Calif.).

Those of skill in the art will appreciate that cells which express the Edg-3 receptor may grown in vitro or may be part of a complex organism such as, for example, a mammal. It is contemplated that the methods of the current invention will be applicable to modulating, e.g., agonizing or antagonizing, Edg-3 receptor activity, regardless of the local environment. In one preferred embodiment, cells that express the Edg-3 receptor are grown in vitro (i.e., are cultured). In another preferred embodiment, cells that express the Edg-3 receptor are in vivo (i.e., are part of a complex organism).

The cells in which the method of the invention may be practiced include, but are not limited to, hepatoma cells, ovarian cells, epithelial cells, fibroblast cells, neuronal cells, cardiac myocytes, carcinoma cells, pheochromocytoma cells, myoblast cells, platelet cells, endothelial cells, keratinocytes and fibrosarcoma cells. More specifically, the cells in which the invention may be practiced include, but are not limited to, OV202 human ovarian cells, HTC rat hepatoma cells, CAOV-3 and SKOV-3 human ovarian cancer cells, MDA-MB-453 breast cancer cells, MDA-MB-231 breast cancer cells, HUVEC, Hela human cervical adenocarcinoam cells, HEK293 human embryonic kidney cells, NIH 3T3 mouse fibroblast cells, A431 human epitheloid carcinoma cells, and HT-1080 human fibrosarcoma cells.

In a second aspect of the invention, an Edg-3 receptor mediated biological activity is modulated in a subject or in an animal model. A therapeutically effective amount of an modulator of the Edg-3 receptor is administered to the subject or animal. Preferably, the subject or animal is in need of such treatment.

The biological activity mediated by the Edg-3 receptor may include, for example, calcium mobilization, VEGF synthesis, IL-8 synthesis, platelet activation, cell migration, phosphoinositide hydrolysis, inhibition of cAMP formation or actin polymerization. Preferably, the biological activity mediated by the Edg-3 receptor also includes, but is not limited to, apoptosis, angiogenesis, wound healing, inflammation, expression of endogenous protein growth factors, cancer invasiveness or atherogenesis. Most preferably, the biological activity mediated by the Edg-3 receptor is cell proliferation, which may lead to enhancement of wound healing; alternatively, it may lead ovarian cancer, peritoneal cancer, endometrial cancer, cervical cancer, breast cancer, colorectal cancer, uterine cancer, stomach cancer, small intestine cancer, thyroid cancer, lung cancer, kidney cancer, pancreas cancer or prostrate cancer. In one embodiment, cell proliferation is stimulated by S1P.

In another embodiment, the biological activity mediated by the Edg-3 receptor may include increasing fatty acids levels (e.g., free fatty acids and lyso-phosphatidylcholine) which may lead to acute lung diseases, such as adult respiratory distress syndrome ("ARDS") and acute inflammatory exacerbation of chronic lung diseases like asthma.

In yet another embodiment, the present invention provides methods for using Edg-3 antagonists in treating or preventing disorders such as, but not limited to, vasoconstriction in cerebral arteries, autoimmune and related immune disorders, including, but not limited to, systemic lupus erythematosus (SLE), rheumatoid arthritis, non-glomerular nephrosis, psoriasis, chronic active hepatitis, ulcerative colitis, Crohn's disease, Behçet's disease, chronic glomerulonephritis, chronic thrombocytopenic purpura, and autoimmune hemolytic anemia. Additionally, Edg-3 antagonists can also be used in organ transplantation. Without intending to be bound by any particular mechanism or theory of action, Edg-3 antagonists are believed to be potentially effective immunosuppresive agents because activated T cells express the Edg-3 receptor.

In yet another embodiment, Edg-3 agonists and antagonists can be used to treat vascular occlusive disorders. For example, activation of Edg-3 receptors by using an Edg-3 agonist can result in increased vasoconstriction, which is beneficial in conditions such as migraine headaches. Inhibition of Edg-3 by an Edg3 antagonist can be beneficial in conditions such as a stroke, a subarachnoid hemorrhage, or a vasospasm such as a cerebral vasospasm.

In certain aspects, the modulator exhibits inhibitory selectivity for the Edg-3 receptor. In one embodiment, the modulator exhibits at least about 5 fold inhibitory selectivity for Edg-3 relative to other Edg receptors. Inhibitory selectivity can be measured by assays such as a calcium mobilization assay or a migration and/or invasion assay or a proliferation assay, for example, as described in Section 6.4 (Example 4), 6.6 (Example 6) and 6.7 (Example 7) respectively. Other assays suitable for determining inhibitory selectivity would be known to one of skill in the art. Preferred assays include the calcium mobilization assay of Section 6.4.

In another embodiment, the modulator exhibits at least about 20 fold inhibitory selectivity for Edg-3 relative to other Edg receptors.

In another embodiment, the modulator exhibits at least about 100 fold inhibitory selectivity for Edg-3 relative to other Edg receptors.

In another embodiment, the modulator exhibits at least about 200 fold inhibitory selectivity for Edg-3 relative to other Edg receptors.

In another embodiment, the modulator exhibits about 5 fold to about 200 fold inhibitory selectivity for Edg-3 relative to other Edg receptors.

In still another embodiment, the modulator exhibits at least about 5 fold inhibitory selectivity for Edg-3 relative to Edg-1, Edg-5, Edg-6 and Edg-8 receptors.

In still another embodiment, the modulator exhibits at least about 20 fold inhibitory selectivity for Edg-3 relative to Edg-1, Edg-5, Edg-6 and Edg-8 receptors.

In still another embodiment, the modulator exhibits at least about 100 fold inhibitory selectivity for Edg-3 relative to Edg-1, Edg-5, Edg-6 and Edg-8 receptors.

In still another embodiment, the modulator exhibits at least about 200 fold inhibitory selectivity for Edg-3 relative to Edg-1, Edg-5, Edg-6 and Edg-8 receptors.

In still another embodiment, the modulator exhibits about 5 fold to about 200 fold inhibitory selectivity for Edg-3 relative to Edg-1, Edg-5, Edg-6 and Edg-8 receptors.

In a preferred embodiment, the modulator of cell proliferation exhibits at least about 5 fold inhibitory selectivity for Edg-3 relative to other Edg receptors.

In another embodiment, the modulator of cell proliferation exhibits at least about 20 fold inhibitory selectivity for Edg-3 relative to other Edg receptors.

In still another embodiment, the modulator of cell proliferation exhibits at least about 5 fold inhibitory selectivity for Edg-3 relative to Edg-1, Edg-5, Edg-6 and Edg-8 receptors.

In still another embodiment, the modulator of cell proliferation exhibits at least about 20 fold inhibitory selectivity for Edg-3 relative to Edg-1, Edg-5, Edg-6 and Edg-8 receptors.

In other aspects, the modulator exhibits stimulatory selectivity for the Edg-3 receptor. In one embodiment, the modulator exhibits at least about 5 fold stimulatory selectivity for Edg-3 relative to other Edg receptors. Stimulatory selectivity can be measured by assays such as a calcium mobilization assay or a migration and/or invasion assay or a proliferation assay, for example, as described in Section 6.4 (Example 4), 6.6 (Example 6) and 6.7 (Example 7) respectively. Other assays suitable for determining stimulatory selectivity would be known to one of skill in the art. Preferred assays include the calcium mobilization assay of Section 6.4.

In another embodiment, the modulator exhibits at least about 20 fold stimulatory selectivity for Edg-3 relative to other Edg receptors.

In another embodiment, the modulator exhibits at least about 100 fold stimulatory selectivity for Edg-3 relative to other Edg receptors.

In another embodiment, the modulator exhibits at least about 200 fold stimulatory selectivity for Edg-3 relative to other Edg receptors.

In another embodiment, the modulator exhibits at least about 200 fold stimulatory selectivity for Edg-3 relative to other Edg receptors.

In still another embodiment, the modulator exhibits about 5 fold to about 200 fold stimulatory selectivity for Edg-3 relative to other Edg receptors.

In still another embodiment, the modulator exhibits at least about 5 fold stimulatory selectivity for Edg-3 relative to Edg-1, Edg-5, Edg-6 and Edg-8 receptors.

In still another embodiment, the modulator exhibits at least about 20 fold stimulatory selectivity for Edg-3 relative to Edg-1, Edg-5, Edg-6 and Edg-8 receptors.

In still another embodiment, the modulator exhibits at least about 100 fold stimulatory selectivity for Edg-3 relative to Edg-1, Edg-5, Edg-6 and Edg-8 receptors.

In still another embodiment, the modulator exhibits at least about 200 fold stimulatory selectivity for Edg-3 relative to Edg-1, Edg-5, Edg-6 and Edg-8 receptors.

In still another embodiment, the modulator exhibits about 5 fold to about 200 fold stimulatory selectivity for Edg-3 relative to Edg-1, Edg-5, Edg-6 and Edg-8 receptors.

In a preferred embodiment, the modulator of cell proliferation exhibits at least about 5 fold stimulatory selectivity for Edg-3 relative to other Edg receptors.

In another embodiment, the modulator of cell proliferation exhibits at least about 20 fold stimulatory selectivity for Edg-3 relative to other Edg receptors.

In still another embodiment, the modulator of cell proliferation exhibits at least about 5 fold stimulatory selectivity for Edg-3 relative to Edg-1, Edg-5, Edg-6 and Edg-8 receptors.

In still another embodiment, the modulator of cell proliferation exhibits at least about 20 fold stimulatory selectivity for Edg-3 relative to Edg-1, Edg-5, Edg-6 and Edg-8 receptors.

In certain embodiments, the Edg-3 modulator is not a lipid. In certain embodiments, the modulator of Edg-3 receptor mediated biological activity does not contain a phosphate group such as a phosphoric acid, a cyclic phosphate ester or a linear phosphate ester. In certain embodiments, the modulator of the Edg-3 receptor is not a phospholipid. The term "phospholipid" includes all phosphate (both phosphate esters and phosphoric acids) containing glycerol derivatives with an alkyl chain of greater 10 carbon atoms or greater, dioctyl glycerol, any N-acyl ethanolamide phosphate derivative (both phosphate esters and phosphoric acids), LPA, S1P or any of their analogues (both phosphate esters and phosphoric acids) (see, e.g., Bandoh, et al., 2000, *FEBS Lett.* 428, 759; Bittman et al., 1996, *J. Lipid Research* 391; Lilliom et al., 1996, *Molecular Pharmacology* 616, Hooks et al., 1998, *Molecular Pharmacology* 188; Fischer et al., 1998, *Molecular Pharmacology* 979; Heise et al., 2001, *Molecular Pharmacology* 1173; Hopper et al., 1999, *J. Med. Chem.* 42 (6):963–970; Tigyi et al., 2001, *Molecular Pharmacology* 1161).

In certain embodiments, the modulator is also not a compound of structural formula (IV):

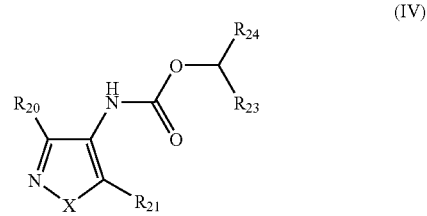

(IV)

or a pharmaceutically available salt thereof, wherein:

X is O or S;

$R_{20}$ is alkyl, substituted alkyl, aryl, substituted aryl or halo;

$R_{21}$ is alkyl, substituted alkyl, aryl, substituted aryl, heteroaryl or substituted heteroaryl;

$R_{23}$ is hydrogen, alkyl or substituted alkyl;

$R_{24}$ is aryl, substituted aryl, heteroaryl or substituted heteroaryl;

or alternatively $R_{23}$ and $R_{24}$ form a cycloalkyl ring (International Application No: WO 01/60819).

In certain embodiments, the modulator is not any compound of the formula below:

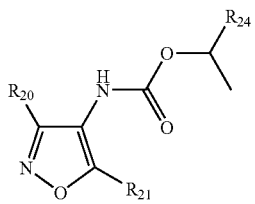

wherein $R_{20}$, $R_{21}$ and $R_{24}$ are as previously defined. In yet another embodiment the modulator is not any compound disclosed in International Application No: WO 01/60819.

In certain embodiments, the modulator can be an agonist of the Edg-3 receptor. The agonist can be a weaker agonist than the natural agonist and may compete with the natural agonist for the binding site. In other embodiments, the modulator can be an antagonist of the Edg-3 receptor.

In certain aspects, the Edg-3 modulator can be a biomolecule such as a nucleic acid, protein, (e.g., an enzyme, an antibody, or a soluble Edg-3 receptor polypeptide) or oligosaccharide or any combination thereof. Alternatively, the Edg-3 modulator may be oligomers or monomers of the above biomolecules such as amino acids, peptides, monosaccharides, disaccharides, nucleic acid monomers, dimers, etc., or any combination thereof. The Edg-3 modulator may also be a synthetic polymer or any combination of synthetic polymer with biomolecules including monomers or oligomers of biomolecules.

The Edg-3 modulator may also be a small organic molecule. In certain embodiments, the Edg-3 modulator can be an organic molecule of molecular weight less than 750 daltons. In other embodiments, the molecular weight can be about 200 to about 1000 daltons. In other embodiments, the molecular weight can be about 200 to about 750 daltons. In yet other embodiments, the molecular weight can be about 200 to about 600 daltons. In certain preferred embodiments, the molecular weight is about 300 to about 500 daltons. In certain embodiments, the small organic molecule can be orally administered to a subject. In other embodiments, the small organic molecule is capable of crossing the blood-brain barrier.

Without wishing to be bound by any particular theory or understanding, the modulator may, for example, facilitate inhibition of the Edg-3 receptor through direct binding to the LPA binding site of the receptor, binding at some other site of the Edg-3 receptor, interfering with Edg-3 or LPA biosynthesis, covalently modifying either the LPA or the Edg-3 receptor, or otherwise interfering with Edg-3 mediated signal transduction.

In one embodiment, the modulator binds to the Edg-3 receptor with a binding constant between about 10 μM and about 1 fM. In another embodiment, the modulator binds to the Edg-3 receptor with a binding constant between about 10 μM and about 1 nM. In another embodiment, the modulator binds to the Edg-3 receptor with a binding constant between about 1 μM and about 1 nM. In another embodiment, the modulator binds to the Edg-3 receptor with a binding constant between about 100 nM and about 1 nM. In another embodiment, the modulator binds to the Edg-3 receptor with a binding constant between about 10 nM and about 1 nM. Preferably, the modulator binds to the Edg-3 receptor with a binding constant better (i.e., less) than about 10 nM.

In certain embodiments, the modulator is a compound of structural formula (I):

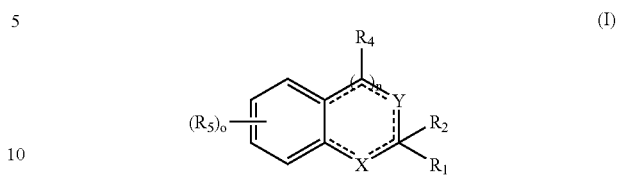

or a pharmaceutically available solvate or hydrate thereof, wherein:

n=0 or 1;

o is 0, 1, 2, 3 or 4;

X is C, $NR^7$ O or S;

Y is C, $NR^8$ O or S;

$R_1$ is either absent or hydrogen, alkyl, substituted alkyl, acyl, substituted acyl, acylamino, substituted acylamino, alkylamino, substituted alkylamino, alkylthio, substituted alkylthio, alkoxy, substituted alkoxy, alkoxycarbonyl, substituted alkoxycarbonyl, alkylarylamino, substituted alkylarylamino, arylalkyloxy, substituted arylalkyloxy, amino, aryl, substituted aryl, arylalkyl, substituted arylalkyl, arylamino, substituted arylamino, arylsulfonyl, substituted arylsulfonyl, carboxy, carbamoyl, substituted carbamoyl, cycloalkyl, substituted cycloalkyl, cycloheteroalkyl, substituted cycloheteroalkyl, dialkylamino, substituted dialkylamino, heteroaryloxy, substituted heteroaryloxy, heteroaryl, substituted heteroaryl, heteroalkyl, or substituted heteroalkyl;

$R_2$, $R_3$ and $R_4$ are independently hydrogen, alkyl, substituted alkyl, acyl, substituted acyl, acylamino, substituted acylamino, alkylamino, substituted alkylamino, alkylthio, substituted alkylthio, alkoxy, substituted alkoxy, alkoxycarbonyl, substituted alkoxycarbonyl, alkylarylamino, substituted alkylarylamino, arylalkyloxy, substituted arylalkyloxy, amino, aryl, substituted aryl, arylalkyl, substituted arylalkyl, arylamino, substituted arylamino, arylsulfonyl, substituted arylsulfonyl, carboxy, carbamoyl, substituted carbamoyl, cycloalkyl, substituted cycloalkyl, cycloheteroalkyl, substituted cycloheteroalkyl, dialkylamino, substituted dialkylamino, heteroaryloxy, substituted heteroaryloxy, heteroaryl, substituted heteroaryl, heteroalkyl, or substituted heteroalkyl;

each $R_5$ is independently, alkyl, substituted alkyl, acyl, substituted acyl, acylamino, substituted acylamino, alkylamino, substituted alkylamino, alkylthio, substituted alkylthio, alkoxy, substituted alkoxy, alkoxycarbonyl, substituted alkoxycarbonyl, alkylarylamino, substituted alkylarylamino, arylalkyloxy, substituted arylalkyloxy, amino, aryl, substituted aryl, arylalkyl, substituted arylalkyl, arylsulfonyl, substituted arylsulfonyl, azido, carboxy, carbamoyl, substituted carbamoyl, carboxyl, cyano, cycloalkyl, substituted cycloalkyl, cycloheteroalkyl, substituted cycloheteroalkyl, dialkylamino, substituted dialkylamino, halo, heteroaryloxy, substituted heteroaryloxy, heteroaryl, substituted heteroaryl, heteroalkyl, substituted heteroalkyl, hydroxyl, nitro or thio; and $R_7$ and $R_8$ are independently absent, hydrogen, alkyl, substituted alkyl, acyl or substituted acyl.

In other embodiments, the modulator is a compound of structural formula (VI):

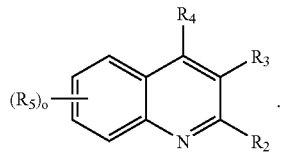

In one embodiment, $R_1$ is either absent or hydrogen, acyl, substituted acyl, acylamino, substituted acylamino, alkoxycarbonyl, substituted alkoxycarbonyl, alkylamino, substituted alkylamino, alkylarylamino, substituted alkylarylamino, arylamino, substituted arylamino, arylalkyloxy, substituted arylalkyloxy, carbamoyl, substituted carbamoyl, dialkylamino, substituted dialkylamino, heteroalkyl, or substituted heteroalkyl. Preferably, $R_1$ is either absent or acylamino, substituted acylamino, alkoxycarbonyl, substituted alkoxycarbonyl, arylamino substituted arylamino, or carbamoyl, substituted carbamoyl. More preferably, $R_1$ is either absent or acylamino, substituted acylamino, arylamino or substituted arylamino.

In another embodiment, $R_2$, $R_3$ and $R_4$ are independently alkyl, substituted alkyl, acyl, substituted acyl, acylamino, substituted acylamino, alkylamino, substituted alkylamino, alkoxycarbonyl, substituted alkoxycarbonyl, alkylarylamino, substituted alkylarylamino, aryl, substituted aryl, arylalkyl, substituted arylalkyl, arylamino, substituted arylamino, carbamoyl, substituted carbamoyl, dialkylamino, substituted dialkylamino, heteroaryl, substituted heteroaryl, heteroalkyl, or substituted heteroalkyl. Preferably, $R_2$, $R_3$ and $R_4$ are independently alkyl, substituted alkyl, acylamino, substituted acylamino, aryl, substituted aryl, arylamino, substituted arylamino, carbamoyl or substituted carbamoyl. More preferably, $R_2$, $R_3$ and $R_4$ are independently alkyl, substituted acylamino, aryl, substituted arylamino or substituted carbamoyl.

In another embodiment, each $R_5$ is independently, alkyl, substituted alkyl, alkoxy, substituted alkoxy, alkoxycarbonyl, substituted alkoxycarbonyl, amino, aryl, substituted aryl, azido, carboxy, carbamoyl, substituted carbamoyl, cyano, halo, hydroxyl, nitro or thio. Preferably, each $R_5$ is independently, alkyl, substituted alkyl, alkoxy, substituted alkoxy, amino, azido, carboxy, carbamoyl, substituted carbamoyl, cyano, halo, hydroxyl, nitro or thio. Preferably, $R_7$ and $R_8$ are independently absent, hydrogen, alkyl.

In still other embodiments, the modulator is a compound of structural formula (II):

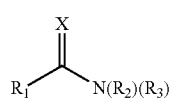

or a pharmaceutically available solvate or hydrate thereof, wherein; each of $R_1$, $R_2$ and $R_3$ is independently —H, -halo, —NO$_2$, —CN, —C(R$_5$)$_3$, —(CH$_2$)$_m$OH, —N(R$_5$)(R$_5$), —O(CH$_2$)$_m$R$_5$, —C(O)R$_5$, —C(O)NR$_5$R$_5$, —C(O)NH(CH$_2$)$_m$(R$_5$), —OCF$_3$, -benzyl, —CO$_2$CH(R$_5$)(R$_5$), —(C$_1$–C$_{10}$)alkyl, —(C$_2$–C$_{10}$)alkenyl, —(C$_2$–C$_{10}$)alkynyl, —(C$_3$–C$_{10}$)cycloalkyl, —(C$_8$–C$_{14}$)bicycloalkyl, —(C$_5$–C$_{10}$)cycloalkenyl, —(C$_5$)heteroaryl, —(C$_6$)heteroaryl, —(C$_5$–C$_{10}$)heteroaryl, -naphthyl, —(C$_3$–C$_{10}$)heterocycle, —CO$_2$(CH$_2$)$_m$R$_5$, —N(OH)aryl, —NHC(O)R$_5$, —NHC(O)OR$_5$, —NHC(O)NHR$_5$, -heterocylcoalkyl, —(C$_1$–C$_{10}$)alkylNHC(O)(CH$_2$)$_m$R$_5$, —(C$_1$–C$_{10}$)alkylNR$_5$R$_5$, —OC(O)(CH$_2$)$_m$CHR$_5$R$_5$, —CO$_2$(CH$_2$)$_m$CHR$_5$R$_5$, —OC(O)OR$_5$, —SR$_5$, —S(O)R$_5$, —S(O)$_2$R$_5$, —S(O)$_2$NHR$_5$, or

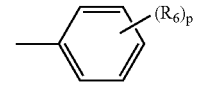

$R_3$ is —H —C(R$_5$)$_3$, —(CH$_2$)$_m$OH, —C(O)R$_5$, —C(O)NR$_5$R$_5$, —C(O)NH(CH$_2$)$_m$(R$_5$), -benzyl, —CO$_2$CH(R$_5$)(R$_5$), —(C$_1$–C$_{10}$)alkyl, —(C$_2$–C$_{10}$)alkenyl, —(C$_2$–C$_{10}$)alkynyl, —(C$_3$–C$_{10}$)cycloalkyl, —(C$_8$–C$_{14}$)bicycloalkyl, —(C$_5$–C$_{10}$)cycloalkenyl, —(C$_5$)heteroaryl, —(C$_6$)heteroaryl, —(C$_5$–C$_{10}$)heteroaryl, -naphthyl, —(C$_3$–C$_{10}$)heterocycle, —CO$_2$(CH$_2$)$_m$R$_5$, —N(OH)aryl, —NHC(O)R$_5$, —NHC(O)OR$_5$, —NHC(O)NHR$_5$, —N=C(aryl), -heterocylcoalkyl, —(C$_1$–C$_{10}$)alkylNHC(O)(CH$_2$)$_m$R$_5$, —(C$_1$–C$_{10}$)alkylNR$_5$R$_5$, —OC(O)(CH$_2$)$_m$CHR$_5$R$_5$, —CO$_2$(CH$_2$)$_m$CHR$_5$R$_5$, —OC(O)OR$_5$, —SR$_5$, —S(O)R$_5$, —S(O)$_2$R$_5$, —S(O)$_2$NHR$_5$, or

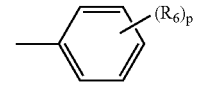

wherein;

each $R_5$ and $R_6$ is independently -halo, —NO$_2$, —CN, —OH, —CO$_2$H, —N(C$_1$–C$_{10}$)alkyl(C$_1$–C$_{10}$)alkyl, —O(C$_1$–C$_{10}$)alkyl, —C(O)(C$_1$–C$_{10}$)alkyl, —C(O)NH(CH$_2$)$_m$(C$_1$–C$_{10}$)alkyl, —OCF$_3$, -benzyl, —CO$_2$(CH$_2$)$_m$CH((C$_1$–C$_{10}$)alkyl (C$_1$–C$_{10}$)alkyl), —CO$_2$(C$_1$–C$_{10}$)alkyl, —(C$_1$–C$_{10}$)alkyl, —(C$_2$–C$_{10}$)alkenyl, —(C$_2$–C$_{10}$)alkynyl, —(C$_3$–C$_{10}$)cycloalkyl, —(C$_8$–C$_{14}$)bicycloalkyl, —(C$_5$–C$_{10}$)cycloalkenyl, —(C$_5$)heteroaryl, —(C$_6$)heteroaryl, -phenyl, naphthyl, —(C$_3$–C$_{10}$)heterocycle, —CO$_2$(CH$_2$)$_m$(C$_1$–C$_{10}$)alkyl, —CO$_2$(CH$_2$)$_m$H, —NHC(O)(C$_1$–C$_{10}$)alkyl, —NHC(O)NH (C$_1$–C$_{10}$)alkyl, —NH(aryl), —N=C(aryl), —OC(O)O (C$_1$–C$_{10}$)alkyl, or —SO$_2$NH$_2$;

X is O, S, C(R$_5$)(R$_5$) or N(R$_5$);

$R_1$, $R_2$ or $R_3$ taken in combination can form one or more substituted or unsubstituted 5 or 6 membered cyclic or heterocyclic rings or a 6-membered aromatic ring;

each m is independently an integer ranging from 0 to 8; and each p is independently an integer ranging from 0 to 5.

In another embodiment, the modulator is a compound of structural formula (VII):

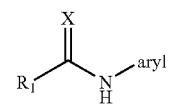

or a pharmaceutically available solvate or hydrate thereof, wherein:

R₁ is hydrogen, alkyl, substituted alkyl, acylamino, substituted acylamino, alkylamino, substituted alkylamino, alkylthio, substituted alkylthio, alkoxy, substituted alkoxy, alkylarylamino, substituted alkylarylamino, amino, arylalkyloxy, substituted arylalkyloxy, aryl, substituted aryl, arylamino, substituted arylamino, arylalkyl, substituted arylalkyl, dialkylamino, substituted alkyl amino, cycloalkyl, substituted cycloalkyl, cycloheteroalkyl, substituted cycloheteroalkyl, heteroaryloxy, substituted heteroaryloxy, heteroaryl, substituted heteroaryl, heteroalkyl, substituted heteroalkyl sulfonylamino or substituted sulfonylamino; and X=O or S.

In yet other embodiments, the Edg-3 receptor modulator is a compound of structural formula (VIII):

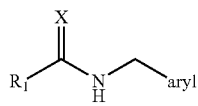

(VIII)

or a pharmaceutically available solvate or hydrate thereof, wherein:

R₁ is hydrogen, alkyl, substituted alkyl, acylamino, substituted acylamino, alkylamino, substituted alkylamino, alkylthio, substituted alkylthio, alkoxy, substituted alkoxy, alkylarylamino, substituted alkylarylamino, amino, arylalkyloxy, substituted arylalkyloxy, aryl, substituted aryl, arylamino, substituted arylamino, arylalkyl, substituted arylalkyl, dialkylamino, substituted alkyl amino, cycloalkyl, substituted cycloalkyl, cycloheteroalkyl, substituted cycloheteroalkyl, heteroaryloxy, substituted heteroaryloxy, heteroaryl, substituted heteroaryl, heteroalkyl, substituted heteroalkyl sulfonylamino or substituted sulfonylamino; and

X=O.

In yet other embodiments, the Edg-3 receptor modulator has the structural formula (III):

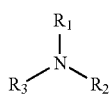

(III)

or a pharmaceutically available solvate or hydrate thereof, wherein;

each of $R_1$, $R_2$ and $R_3$ is independently —H, -halo, —NO₂, —CN, —C(R₅)₃, —(CH₂)$_m$OH, —N(R₅)(R₅), —O(CH₂)$_m$R₅, —C(O)R₅, —C(O)NR₅R₅, —C(O)NH(CH₂)(R₅), —OCF₃, -benzyl, —CO₂CH(R₅)(R₅), —(C₁–C₁₀)alkyl, —(C₂–C₁₀)alkenyl, —(C₂–C₁₀)alkynyl, —(C₃–C₁₀)cycloalkyl, —(C₈–C₁₄)bicycloalkyl, —(C₅–C₁₀)cycloalkenyl, —(C₅)heteroaryl, —(C₆)heteroaryl, —(C₅–C₁₀)heteroaryl, -naphthyl, —(C₃–C₁₀)heterocycle, —CO₂(CH₂)$_m$R₅, —N(OH)aryl, —NHC(O)R₅, —NHC(O)OR₅, —NHC(O)NHR₅, -heterocylcoalkyl, —C(S)N(R₅)(R₅), —(C₁–C₁₀) alkylNHC(O)(CH₂)$_m$R₅, —(C₁–C₁₀)alkylNR₅R₅, —OC(O)(CH₂)$_m$CHR₅R₅, —CO₂(CH₂)$_m$CHR₅R₅, —OC(O)OR₅, —SR₅, —S(O)R₅, —S(O)₂R₅, —S(O)₂NHR₅, or

$R_3$ is —H —C(R₅)₃, —(CH₂)$_m$OH, —C(O)R₅, —C(O)NR₅R₅, —C(O)NH(CH₂)$_m$(R₅), -benzyl, —CO₂CH(R₅)(R₅), —(C₁–C₁₀)alkyl, —(C₂–C₁₀)alkenyl, —(C₂–C₁₀)alkynyl, —(C₃–C₁₀)cycloalkyl, —(C₈–C₁₄)bicycloalkyl, —(C₅–C₁₀)cycloalkenyl, —(C₅)heteroaryl, —(C₆)heteroaryl, —(C₅–C₁₀)heteroaryl, -naphthyl, —(C₃–C₁₀)heterocycle, —CO₂(CH₂)$_m$R₅, —N(OH)aryl, —NHC(O)R₅, —NHC(O)OR₅, —NHC(O)NHR₅, —N=C(aryl), -heterocylcoalkyl, —(C₁–C₁₀)alkylNHC(O)(CH₂)$_m$R₅, —(C₁–C₁₀) alkylNR₅R₅, —OC(O)(CH₂)$_m$CHR₅R₅, —CO₂(CH₂)$_m$CHR₅R₅, —OC(O)OR₅, —SR₅, —S(O)R₅, —S(O)₂R₅, —S(O)₂NHR₅, or

wherein;

each R₅ and R₆ is independently —H, -halo, —NO₂, —CN, —OH, —CO₂H, —N(C₁–C₁₀)alkyl(C₁–C₁₀)alkyl, —O(C₁–C₁₀)alkyl, —C(O)(C₁–C₁₀)alkyl, —C(O)NH (CH₂)$_m$(C₁–C₁₀)alkyl, —OCF₃, -benzyl, —CO₂(CH₂)$_m$CH((C₁–C₁₀)alkyl(C₁–C₁₀)alkyl), —CO₂(C₁–C₁₀)alkyl, —(C₁–C₁₀)alkyl, —(C₂–C₁₀)alkenyl, —(C₂–C₁₀)alkynyl, —(C₃–C₁₀)cycloalkyl, —(C₈–C₁₄)bicycloalkyl, —(C₅–C₁₀)cycloalkenyl, —(C₅)heteroaryl, —(C₆)heteroaryl, -phenyl, naphthyl, —(C₃–C₁₀)heterocycle, —CO₂(CH₂)$_m$(C₁–C₁₀)alkyl, —CO₂(CH₂)$_m$H, —NHC(O)(C₁–C₁₀)alkyl, —NHC(O)NH(C₁–C₁₀)alkyl, —NH(aryl), —N=C(aryl), —OC(O)O(C₁–C₁₀)alkyl, or —SO₂NH₂;

X is O, S, or N(R₅);

$R_1$, $R_2$ or $R_3$ taken in combination can form one or more substituted or unsubstituted 5 or 6 membered cyclic or heterocyclic rings or a 6-membered aromatic ring;

two R₆ groups on adjacent carbon atoms can together form a 5 or 6 membered cyclic or heterocyclic ring or a 6-membered aromatic ring;

each m is independently an integer ranging from 0 to 8; and each p is independently an integer ranging from 0 to 5.

In still other embodiments, the Edg-3 receptor modulator is a compound of structural formula (IX):

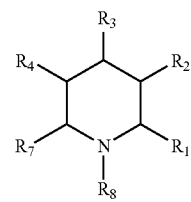

(IX)

or a pharmaceutically available solvate or hydrate thereof, wherein; each of $R_1$, $R_2$, $R_3$, $R_4$, $R_7$ and $R_9$ is independently —H, -halo, —NO$_2$, —CN, —C(R$_5$)$_3$, —(CH$_2$)$_m$OH, —N(R$_5$)(R$_5$), —O(CH$_2$)$_m$R$_5$, —C(O)R$_5$, —C(O)NR$_5$R$_5$, —C(O)NH(CH$_2$)$_m$(R$_5$), —OCF$_3$, -benzyl, —CO$_2$CH(R$_5$)(R$_5$), —(C$_1$–C$_{10}$)alkyl, —(C$_2$–C$_{10}$)alkenyl, —(C$_2$–C$_{10}$)alkynyl, —(C$_3$–C$_{10}$)cycloalkyl, —(C$_8$–C$_{14}$)bicycloalkyl, —(C$_5$–C$_{10}$)cycloalkenyl, —(C$_5$)heteroaryl, —(C$_6$)heteroaryl, —(C$_5$–C$_{10}$)heteroaryl, -naphthyl, —(C$_3$–C$_{10}$)heterocycle, —CO$_2$(CH$_2$)$_m$R$_5$, —N(OH)aryl, —NHC(O)R$_5$, —NHC(O)OR$_5$, —NHC(O)NHR$_5$, -heterocylcoalkyl, —C(S)N(R$_5$)(R$_5$), —(C$_1$–C$_{10}$)alkylNHC(O)(CH$_2$)$_m$R$_5$, —(C$_1$–C$_{10}$)alkylNR$_5$R$_5$, —OC(O)(CH$_2$)$_m$CHR$_5$R$_5$, —CO$_2$(CH$_2$)$_m$CHR$_5$R$_5$, —OC(O)OR$_5$, —SR$_5$, —S(O)R$_5$, —S(O)$_2$R$_5$, —S(O)$_2$NHR$_5$, or

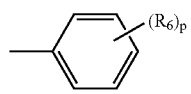

R$_3$ is —H —C(R$_5$)$_3$, —(CH$_2$)$_n$OH, —C(O)R$_5$, —C(O)NR$_5$R$_5$, —C(O)NH(CH$_2$)$_m$(R$_5$), -benzyl, —CO$_2$CH(R$_5$)(R$_5$), —(C$_1$–C$_{10}$)alkyl, —(C$_2$–C$_{10}$)alkenyl, —(C$_2$–C$_{10}$)alkynyl, —(C$_3$–C$_{10}$)cycloalkyl, —(C$_8$–C$_{14}$)bicycloalkyl, —(C$_5$–C$_{10}$)cycloalkenyl, —(C$_5$)heteroaryl, —(C$_6$)heteroaryl, —(C$_5$–C$_{10}$)heteroaryl, -naphthyl, —(C$_3$–C$_{10}$)heterocycle, —CO$_2$(CH$_2$)$_m$R$_5$, —N(OH)aryl, —NHC(O)R$_5$, —NHC(O)OR$_5$, —NHC(O)NHR$_5$, —N=C(aryl), -heterocylcoalkyl, —(C$_1$–C$_{10}$)alkylNHC(O)(CH$_2$)$_m$R$_5$, —(C$_1$–C$_{10}$)alkylNR$_5$R$_5$, —OC(O)(CH$_2$)$_m$CHR$_5$R$_5$, —CO$_2$(CH$_2$)$_m$CHR$_5$R$_5$, —OC(O)OR$_5$, —SR$_5$, —S(O)R$_5$, —S(O)$_2$R$_5$, —S(O)$_2$NHR$_5$, or

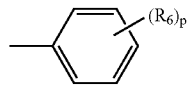

wherein;

each R$_5$ and R$_6$ is independently —H, -halo, —NO$_2$, —CN, —OH, —CO$_2$H, —N(C$_1$–C$_{10}$)alkyl(C$_1$–C$_{10}$)alkyl, —O(C$_1$–C$_{10}$)alkyl, —C(O)(C$_1$–C$_{10}$)alkyl, —C(O)NH(CH$_2$)$_m$(C$_1$–C$_{10}$)alkyl, —OCF$_3$, -benzyl, —CO$_2$(CH$_2$)$_m$CH((C$_1$–C$_{10}$)alkyl(C$_1$–C$_{10}$)alkyl), —CO$_2$(C$_1$–C$_{10}$)alkyl, —(C$_1$–C$_{10}$)alkyl, —(C$_2$–C$_{10}$)alkenyl, —(C$_2$–C$_{10}$)alkynyl, —(C$_3$–C$_{10}$)cycloalkyl, —(C$_8$–C$_{14}$)bicycloalkyl, —(C$_5$–C$_{10}$)cycloalkenyl, —(C$_5$)heteroaryl, —(C$_6$)heteroaryl, -phenyl, naphthyl, —(C$_3$–C$_{10}$)heterocycle, —CO$_2$(CH$_2$)$_m$(C$_1$–C$_{10}$)alkyl, —CO$_2$(CH$_2$)$_m$H, —NHC(O)(C$_1$–C$_{10}$)alkyl, —NHC(O)NH(C$_1$–C$_{10}$)alkyl, —NH(aryl), —N=C(aryl), —OC(O)O(C$_1$–C$_{10}$)alkyl, or —SO$_2$NH$_2$;

X is O, S, or N(R$_5$);

R$_1$ and R$_2$, R$_2$ and R$_3$, R$_3$ and R$_4$, R$_4$ and R$_7$, or R$_7$ and R$_8$ taken in combination can form one or more substituted or unsubstituted 5 or 6 membered cyclic or heterocyclic rings or a 6-membered aromatic ring;

two R$_6$ groups on adjacent carbon atoms can together form a 5 or 6 membered cyclic or heterocyclic ring or a 6-membered aromatic ring;

each m is independently an integer ranging from 0 to 8; and each p is independently an integer ranging from 0 to 5.

Preferred Edg-3 modulators include the following compounds:

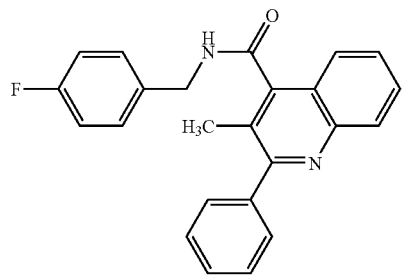

101

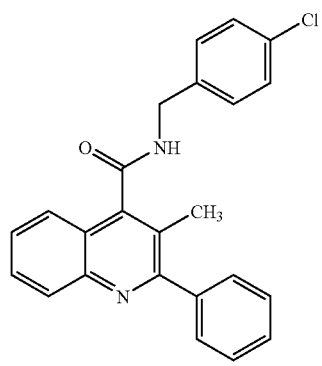

105

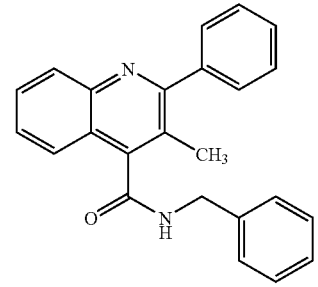

107

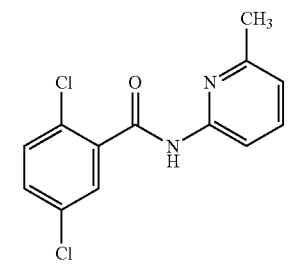

109

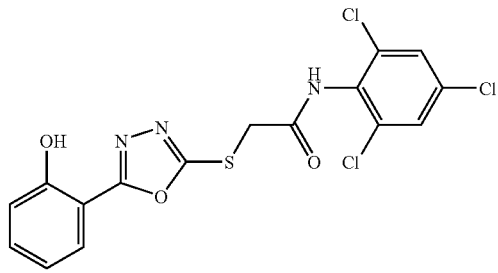

111

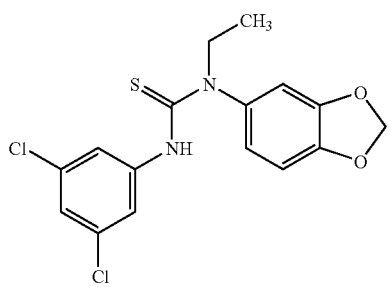

Preferred Edg-3 receptor modulators also include the following compound:

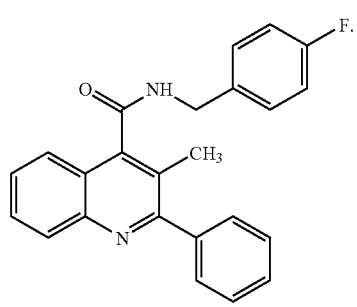

Preferred Edg-3 receptor modulators also include the following compounds:

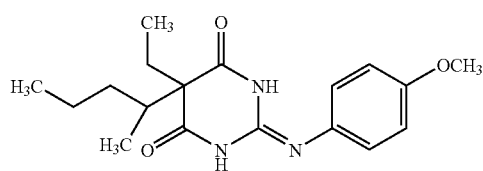

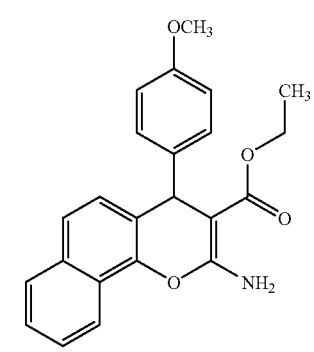

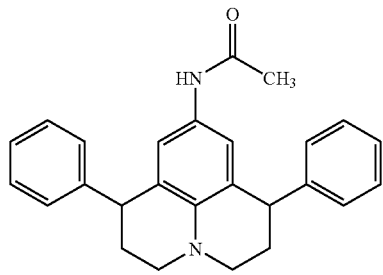

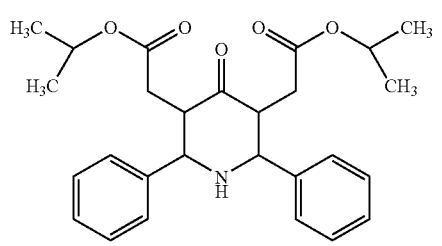

5.3. Synthesis of the Compounds of the Invention

The compounds of the invention may be obtained via the synthetic methods illustrated in Scheme 1. Starting materials useful for preparing compounds of the invention and intermediates thereof are commercially available or can be prepared by well-known synthetic methods. Other methods for synthesis of the compounds described herein are either described in the art or will be readily apparent to the skilled artisan in view of general references well-known in the art (See e.g., Green et al., "Protective Groups in Organic Chemistry", (Wiley, $2^{nd}$ ed. 1991); Harrison et al., "Compendium of Synthetic Organic Methods", Vols. 1–8 (John Wiley and Sons, 1971–1996); "Beilstein Handbook of Organic Chemistry," Beilstein Institute of Organic Chemistry, Frankfurt, Germany; Feiser et al., "Reagents for Organic Synthesis," Volumes 1–17, Wiley Interscience; Trost et al., "Comprehensive Organic Synthesis," Pergamon Press, 1991; "Theilheimer's Synthetic Methods of Organic Chemistry," Volumes 1–45, Karger, 1991; March, "Advanced Organic Chemistry," Wiley Interscience, 1991; Larock "Comprehensive Organic Transformations," VCH Publishers, 1989; Paquette, "Encyclopedia of Reagents for Organic Synthesis," John Wiley & Sons, 1995) and may be used to synthesize the compounds of the invention. Accordingly, the methods presented in Scheme 1 herein are illustrative rather than comprehensive.

The route described in Scheme 1 may used to synthesize compounds of Formula (I).

Scheme 1

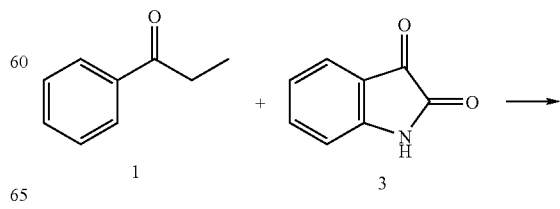

-continued

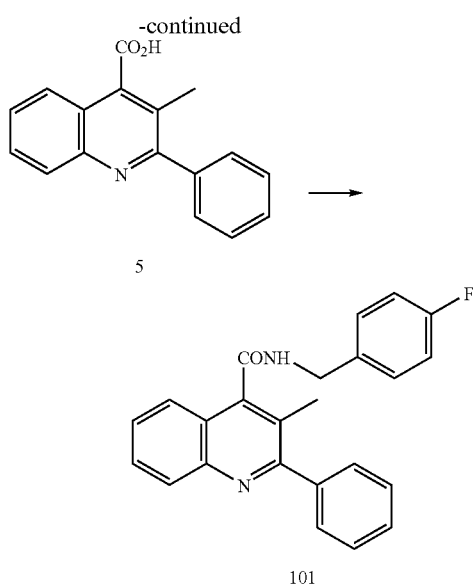

Condensation of propiophenone 1 with isatin 3 (i.e., Pfitzinger reaction, KOH, ethanol, heat) provided quinoline 5, which was then acylated with fluoroamine 101 (i.e., carbodiimide, HOBT) to give amide 101. Those of skill in the art will appreciate that a wide variety of analogues of amide 101 may be made by simply reacting substituted propiophenones with substituted isatins and/or acylating the resulting quinoline with different arylamines.

Illustrative compounds 101, 109, and 111 are commercially available from Specs. Illustrative compounds 107, 113, 115, and 119 are commercially available from Asinex. Illustrative compounds 105 and 117 are commercially available from Chemdiv. Illustrative compound 121 is available from Tripos.

5.4. Therapeutic Uses of the Compounds of the Invention

The compounds and/or compositions of the present invention may be used to prevent and/or treat diseases, including but not limited to, ovarian cancer (Xu et al., 1995, *Biochem. J.* 309 (Pt 3):933–940; Xu et al., 1998, *JAMA* 280 (8): 719–723; Goetzl et al., 1999, *Cancer Res.* 59 (20):5370–5375), peritoneal cancer, endometrial cancer, cervical cancer, breast cancer, colorectal cancer, uterine cancer, stomach cancer, small intestine cancer, thyroid cancer, lung cancer, kidney cancer, pancreas cancer and prostrate cancer; acute lung diseases, adult respiratory distress syndrome ("ARDS"), acute inflammatory exacerbation of chronic lung diseases such as asthma (Chilton et al., 1996, *J Exp Med* 183:2235–45; Arbibe et al., 1998, *J Clin Invest* 102:1152–60) surface epithelial cell injury, (e.g., transcorneal freezing or cutaneous burns (Liliom et al., 1998, *Am. J. Physiol* 274 (4 Pt 1): C1065–C1074)), cardiovascular diseases, (e.g., ischemia (Karliner et al., 2001, *J. Mol. Cell Cardiol.* 33 (9):1713–1717) and athesclerosis (Siess et al., 1999, *Proc. Natl. Acad. Sci. U.S.A* 96 (12):6931–6936; Siess et al., 2000, *IUBMB.B Life* 49 (3):167–171)). In accordance with the invention, a compound and/or composition of the invention is administered to a patient, preferably a human, in need of treatment for a disease which includes but is not limited to, the diseases listed above. Further, in certain embodiments, the compounds and/or compositions of the invention can be administered to a patient, preferably a human, as a preventative measure against diseases or disorders such as those depicted above. Thus, the compounds and/or compositions of the invention can be administered as a preventative measure to a patient having a predisposition, which includes but is not limited to, the diseases listed above. Accordingly, the compounds and/or compositions of the invention may be used for the prevention of one disease or disorder and concurrently treating another disease (e.g., preventing cancer and treating cardiovascular diseases). It is well within the ordinary skill of those in the art to assay and use the compounds and/or compositions of the invention to treat and/or prevent diseases, such as those diseases described above.

In a preferred embodiment, Edg-3 antagonists can be used to treat or prevent disorders such as, but not limited to, vasoconstriction in cerebral arteries, autoimmune and related immune disorders, including, but not limited to, systemic lupus erythematosus (SLE), rheumatoid arthritis, non-glomerular nephrosis, psoriasis, chronic active hepatitis, ulcerative colitis, Crohn's disease, Behçet's disease, chronic glomerulonephritis, chronic thrombocytopenic purpura, and autoimmune hemolytic anemia. Additionally, Edg-3 antagonists can also be used in organ transplantation. In yet another embodiment, Edg-3 agonists and antagonists can be used to treat vascular occlusive disorders. For example, activation of Edg-3 receptors by using an Edg-3 agonist will result in increased vasoconstriction which is beneficial in conditions such as migraine headaches. Inhibition of Edg-3 by an Edg3 antagonist will be beneficial in conditions such as a stroke, a subarachnoid hemorrhage, or a vasospasm such as a cerebral vasospasm. It is well within the capability of those of skill in the art to assay and use the compounds and/or compositions of the invention to treat diseases, such as the diseases listed above.

5.5. Therapeutic/Prophylactic Administration

The compounds and/or compositions of the invention may be advantageously used in medicine, including human medicine. As previously described in Section 5.4 above, compounds and compositions of the invention are useful for the treatment or prevention of diseases, which include but are not limited to, cancers, including, but not limited to, ovarian cancer, peritoneal cancer, endometrial cancer, cervical cancer, breast cancer, colorectal cancer, uterine cancer, stomach cancer, small intestine cancer, thyroid cancer, lung cancer, kidney cancer, pancreas cancer, prostrate cancer, acute lung diseases, including, but not limited to, adult respiratory distress syndrome (ARDS) and acute inflammatory exacerbation of chronic lung diseases such as asthma; surface epithelial cell injury, including, but not limited to, transcorneal freezing or cutaneous burns; cardiovascular diseases, including, but not limited to, ischemia and arthesclerosis.

In a preferred embodiment, Edg-3 antagonists can be used to treat or prevent disorders such as, but not limited to, vasoconstriction in cerebral arteries, autoimmune and related immune disorders, including, but not limited to, systemic lupus erythematosus (SLE), rheumatoid arthritis, non-glomerular nephrosis, psoriasis, chronic active hepatitis, ulcerative colitis, Crohn's disease, Behçet's disease, chronic glomerulonephritis, chronic thrombocytopenic purpura, and autoimmune hemolytic anemia. Additionally, Edg-3 antagonists can also be used in organ transplantation. In yet another embodiment, Edg-3 agonists and antagonists can be used to treat vascular occlusive disorders. For example, activation of Edg-3 receptors by using an Edg-3 agonist will result in increased vasoconstriction which is beneficial in conditions such as migraine headaches. Inhibition of Edg-3 by an Edg3 antagonist will be beneficial in conditions such as a stroke, a subarachnoid hemorrhage, or a vasospasm such as a cerebral vasospasm.

When used to treat or prevent disease or disorders, compounds and/or compositions of the invention may be administered or applied singly, in combination with other agents. The compounds and/or compositions of the invention may also be administered or applied singly, in combination with other pharmaceutically active agents, including other compounds and/or compositions of the invention.

The current invention provides methods of treatment and prophylaxis by administration to a patient of a therapeutically effective amount of a composition or compound of the invention. The patient may be an animal, is more preferably a mammal, and most preferably a human.

The present compounds and/or compositions of the invention, which comprise one or more compounds of the invention, are preferably administered orally. The compounds and/or compositions of the invention may also be administered by any other convenient route, for example, by infusion or bolus injection, by absorption through epithelial or mucocutaneous linings (e.g., oral mucosa, rectal and intestinal mucosa, etc.). Administration can be systemic or local. Various delivery systems are known, (e.g., encapsulation in liposomes, microparticles, microcapsules, capsules, etc.) that can be used to administer a compound and/or composition of the invention. Methods of administration include, but are not limited to, intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. The preferred mode of administration is left to the discretion of the practitioner, and will depend in-part upon the site of the medical condition. In most instances, administration will result in the release of the compounds and/or compositions of the invention into the bloodstream.

In specific embodiments, it may be desirable to administer one or more compounds and/or composition of the invention locally to the area in need of treatment. This may be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of the disease.

In certain embodiments, it may be desirable to introduce one or more compounds and/or compositions of the invention into the central nervous system by any suitable route, including intraventricular, intrathecal and epidural injection. Intraventricular injection may be facilitated by an intraventricular catheter, for example, attached to a reservoir, such as an Ommaya reservoir.

A compound and/or composition of the invention may also be administered directly to the lung by inhalation. For administration by inhalation, a compound and/or composition of the invention may be conveniently delivered to the lung by a number of different devices. For example, a Metered Dose Inhaler ("MDI"), which utilizes canisters that contain a suitable low boiling propellant, (e.g., dichlorodifluoromethane, trichlorofluoromethane, dichlorotetrafluoroethane, carbon dioxide or any other suitable gas) may be used to deliver compounds of the invention directly to the lung.

Alternatively, a Dry Powder Inhaler ("DPI") device may be used to administer a compound and/or composition of the invention to the lung. DPI devices typically use a mechanism such as a burst of gas to create a cloud of dry powder inside a container, which may then be inhaled by the patient. DPI devices are also well known in the art. A popular variation is the multiple dose DPI ("MDDPI") system, which allows for the delivery of more than one therapeutic dose. For example, capsules and cartridges of gelatin for use in an inhaler or insufflator may be formulated containing a powder mix of a compound of the invention and a suitable powder base such as lactose or starch for these systems.

Another type of device that may be used to deliver a compound and/or a composition of the invention to the lung is a liquid spray device. Liquid spray systems use extremely small nozzle holes to aerosolize liquid drug formulations that may then be directly inhaled into the lung.

In one embodiment, a nebulizer is used to deliver a compound and/or composition of the invention to the lung. Nebulizers create aerosols from liquid drug formulations by using, for example, ultrasonic energy to form fine particles that may be readily inhaled (see e.g., Verschoyle et al., *British J. Cancer* 1999, 80, Suppl. 2, 96, which is herein incorporated by reference). Examples of nebulizers include devices supplied by Sheffield/Systemic Pulmonary Delivery Ltd. (See, Armer et al., U.S. Pat. No. 5,954,047; van der Linden et al., U.S. Pat. No. 5,950,619; van der Linden et al., U.S. Pat. No. 5,970,974), Aventis and Batelle Pulmonary Therapeutics.

In another embodiment, an electrohydrodynamic ("EHD") aerosol device is used to deliver a compound and/or composition of the invention to the lung. EHD aerosol devices use electrical energy to aerosolize liquid drug solutions or suspensions (see e.g., Noakes et al., U.S. Pat. No. 4,765,539). EHD aerosol devices may more efficiently deliver drugs to the lung than other pulmonary delivery technologies.

In another embodiment, the compounds of the invention can be delivered in a vesicle, in particular a liposome (see Langer, *Science* 1990, 249:1527–1533; Treat et al, in "Liposomes in the Therapy of Infectious Disease and Cancer," Lopez-Berestein and Fidler (eds.), Liss, New York, pp. 353–365 (1989); see generally "Liposomes in the Therapy of Infectious Disease and Cancer," Lopez-Berestein and Fidler (eds.), Liss, New York, pp. 353–365 (1989)).

In yet another embodiment, the compounds of the invention can be delivered via sustained release systems, preferably oral sustained release systems. In one embodiment, a pump may be used (see Langer, supra; Sefton, 1987, *CRC Crit Ref Biomed. Eng.* 14:201; Saudek et al., *N. Engl. J. Med.* 1989, 321:574).

In another embodiment, polymeric materials can be used (see "Medical Applications of Controlled Release," Langer and Wise (eds.), CRC Pres., Boca Raton, Fla. (1974); "Controlled Drug Bioavailability," Drug Product Design and Performance, Smolen and Ball (eds.), Wiley, New York (1984); Ranger and Peppas, *J. Macromol. Sci. Rev. Macromol Chem.* 1983, 23:61; see also Levy et al., *Science* 1985, 228:190; During et al., *Ann. Neurol.* 1989, 25:351; Howard et al, *J. Neurosurg.* 1989, 71:105). In a preferred embodiment, polymeric materials are used for oral sustained release delivery. In another embodiment, enteric-coated preparations can be used for oral sustained release administration. In still another embodiment, osmotic delivery systems are used for oral sustained release administration (Verma et al., *Drug Dev. Ind. Pharm.* 2000, 26:695–708).

In yet another embodiment, a controlled-release system can be placed in proximity of the target of the compounds and/or composition of the invention, thus requiring only a fraction of the systemic dose (see, e.g, Goodson, in "Medical Applications of Controlled Release," supra, vol. 2, pp. 115–138 (1984)). Other controlled-release systems discussed in Langer, 1990, Science 249:1527–1533 may also be used.

5.6. Compositions of the Invention

The present compositions contain a therapeutically effective amount of one or more compounds of the invention, preferably in purified form, together with a suitable amount of a pharmaceutically acceptable vehicle, so as to provide the form for proper administration to a patient. When administered to a patient, the compounds of the invention and pharmaceutically acceptable vehicles are preferably sterile. Water is a preferred vehicle when the compound of the invention is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents or pH buffering agents. In addition, auxiliary, stabilizing, thickening, lubricating and coloring agents may be used.

Pharmaceutical compositions comprising a compound of the invention may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries, which facilitate processing of compounds of the invention into preparations which can be used pharmaceutically. Proper formulation is dependent upon the route of administration chosen.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable vehicle is a capsule (see e.g., Grosswald et al., U.S. Pat. No. 5,698,155). Other examples of suitable pharmaceutical vehicles have been described in the art (see Remington's Pharmaceutical Sciences, Philadelphia College of Pharmacy and Science, 17th Edition, 1985).

For topical administration compounds of the invention may be formulated as solutions, gels, ointments, creams, suspensions, etc. as are well-known in the art.

Systemic formulations include those designed for administration by injection, e.g., subcutaneous, intravenous, intramuscular, intrathecal or intraperitoneal injection, as well as those designed for transdermal, transmucosal, oral or pulmonary administration. Systemic formulations may be made in combination with a further active agent that improves mucociliary clearance of airway mucus or reduces mucous viscosity. These active agents include, but are not limited to, sodium channel blockers, antibiotics, N-acetyl cysteine, homocysteine and phospholipids.

In a preferred embodiment, the compounds of the invention are formulated in accordance with routine procedures as a composition adapted for intravenous administration to human beings. Typically, compounds of the invention for intravenous administration are solutions in sterile isotonic aqueous buffer. For injection, a compound of the invention may be formulated in aqueous solutions, preferably in physiologically compatible buffers such as Hanks' solution, Ringer's solution, or physiological saline buffer. The solution may contain formulatory agents such as suspending, stabilizing and/or dispersing agents. When necessary, the compositions may also include a solubilizing agent. Compositions for intravenous administration may optionally include a local anesthetic such as lignocaine to ease pain at the site of the injection. Generally, the ingredients are supplied either separately or mixed together in unit dosage form, for example, as a lyophilized powder or water free concentrate in a hermetically sealed container such as an ampoule or sachette indicating the quantity of active agent. When the compound of the invention is administered by infusion, it can be dispensed, for example, with an infusion bottle containing sterile pharmaceutical grade water or saline. When the compound of the invention is administered by injection, an ampoule of sterile water for injection or saline can be provided so that the ingredients may be mixed prior to administration.

For transmucosal administration, penetrants appropriate to the barrier to be permeated are used in the formulation. Such penetrants are generally known in the art.

Compositions for oral delivery may be in the form of tablets, lozenges, aqueous or oily suspensions, granules, powders, emulsions, capsules, syrups, or elixirs, for example. Orally administered compositions may contain one or more optionally agents, for example, sweetening agents such as fructose, aspartame or saccharin; flavoring agents such as peppermint, oil of wintergreen, or cherry coloring agents and preserving agents, to provide a pharmaceutically palatable preparation. Moreover, where in tablet or pill form, the compositions may be coated to delay disintegration and absorption in the gastrointestinal tract, thereby providing a sustained action over an extended period of time. Selectively permeable membranes surrounding an osmotically active driving compound are also suitable for orally administered compounds of the invention. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles are preferably of pharmaceutical grade.

For oral liquid preparations such as, for example, suspensions, elixirs and solutions, suitable carriers, excipients or diluents include water, saline, alkyleneglycols (e.g., propylene glycol), polyalkylene glycols (e.g., polyethylene glycol) oils, alcohols, slightly acidic buffers between pH 4 and pH 6 (e.g., acetate, citrate, ascorbate at between about 5.0 mM to about 50.0 mM, etc). Additionally, flavoring agents, preservatives, coloring agents, bile salts, acylcarnitines and the like may be added.

For buccal administration, the compositions may take the form of tablets, lozenges, etc. formulated in conventional manner.

Liquid drug formulations suitable for use with nebulizers and liquid spray devices and EHD aerosol devices will typically include a compound of the invention with a pharmaceutically acceptable vehicle. Preferably, the pharmaceutically acceptable vehicle is a liquid such as alcohol, water, polyethylene glycol or a perfluorocarbon. Optionally, another material may be added to alter the aerosol properties of the solution or suspension of compounds of the invention. Preferably, this material is liquid such as an alcohol, glycol, polyglycol or a fatty acid. Other methods of formulating liquid drug solutions or suspension suitable for use in aerosol devices are known to those of skill in the art (see, e.g., Biesalski, U.S. Pat. No. 5,112,598; Biesalski, U.S. Pat. No. 5,556,611).

A compound of the invention may also be formulated in rectal or vaginal compositions such as suppositories or retention enemas, e.g., containing conventional suppository bases such as cocoa butter or other glycerides.

In addition to the formulations described previously, a compound of the invention may also be formulated as a depot preparation. Such long acting formulations may be administered by implantation (e.g., subcutaneously or intramuscularly) or by intramuscular injection. Thus, for example, a compound of the invention may be formulated with suitable polymeric or hydrophobic materials (e.g., as an emulsion in an acceptable oil) or ion exchange resins, or as sparingly soluble derivatives, for example, as a sparingly soluble salt.

When a compound of the invention is acidic, it may be included in any of the above-described formulations as the free acid, a pharmaceutically acceptable salt, a solvate or hydrate. Pharmaceutically acceptable salts substantially retain the activity of the free acid, may be prepared by reaction with bases and tend to be more soluble in aqueous and other protic solvents than the corresponding free acid form.

5.7. Methods of Use and Doses

A compound of the invention, or compositions thereof, will generally be used in an amount effective to achieve the intended purpose. The compounds of the invention or compositions thereof, are administered or applied in a therapeutically effective amount for use to treat or prevent diseases or disorders including but not limited to, ovarian cancer, peritoneal cancer, endometrial cancer, cervical cancer, breast cancer, colorectal cancer, uterine cancer, stomach cancer, small intestine cancer, thyroid cancer, lung cancer, kidney cancer, pancreas cancer, prostrate cancer, acute lung diseases, (e.g., adult respiratory distress syndrome (ARDS) and asthma) surface epithelial cell injury (e.g., transcorneal freezing and cutaneous burns) and cardiovascular diseases such as ischemia and arthesclerosis.

Compounds of the invention and compositions thereof are administered and/or applied in a therapeutically effective amount. The amount of a compound of the invention that will be effective in the treatment of a particular disorder or condition disclosed herein will depend on the nature of the disorder or condition, and can be determined by standard clinical techniques known in the art as previously described. In addition, in vitro or in vivo assays may optionally be employed to help identify optimal dosage ranges. The amount of a compound of the invention administered will, of course, be dependent on, among other factors, the subject being treated, the weight of the subject, the severity of the affliction, the manner of administration and the judgment of the prescribing physician.

For example, the dosage may be delivered in a pharmaceutical composition by a single administration, by multiple applications or controlled release. In a preferred embodiment, the compounds of the invention are delivered by oral sustained release administration. Preferably, in this embodiment, the compounds of the invention are administered twice per day (more preferably, once per day). Dosing may be repeated intermittently, may be provided alone or in combination with other drugs and may continue as long as required for effective treatment of the disease state or disorder.

Suitable dosage ranges for oral administration are dependent on the potency of the but are generally about 0.001 mg to about 200 mg of a compound of the invention per kilogram body weight. Dosage ranges may be readily determined by methods known to the skilled artisan.

Suitable dosage ranges for intravenous (i.v.) administration are about 0.01 mg to about 100 mg per kilogram body weight. Suitable dosage ranges for intranasal administration are generally about 0.01 mg/kg body weight to about 1 mg/kg body weight. Suppositories generally contain about 0.01 milligram to about 50 milligrams of a compound of the invention per kilogram body weight and comprise active ingredient in the range of about 0.5% to about 10% by weight. Recommended dosages for intradermal, intramuscular, intraperitoneal, subcutaneous, epidural, sublingual or intracerebral administration are in the range of about 0.001 mg to about 200 mg per kilogram of body weight. Effective doses may be extrapolated from dose-response curves derived from in vitro or animal model test systems. Such animal models and systems are well known in the art.

The compounds of the invention are preferably assayed in vitro and in vivo, for the desired therapeutic or prophylactic activity, prior to use in humans. For example, in vitro assays can be used to determine whether administration of a specific compound of the invention or a combination of compounds of the invention is preferred for reducing convulsion. The compounds of the invention may also be demonstrated to be effective and safe using animal model systems.

Preferably, a therapeutically effective dose of a compound of the invention described herein will provide therapeutic benefit without causing substantial toxicity. Toxicity of compounds of the invention may be determined using standard pharmaceutical procedures and may be readily ascertained by the skilled artisan. The dose ratio between toxic and therapeutic effect is the therapeutic index. A compound of the invention will preferably exhibit particularly high therapeutic indices in treating disease and disorders. The dosage of a compound of the inventions described herein will preferably be within a range of circulating concentrations that include an effective dose with little or no toxicity.

5.8. Combination Therapy

In certain embodiments, the compounds of the invention can be used in combination therapy with at least one other therapeutic agent. The compound of the invention and the other therapeutic agent can act additively or, more preferably, synergistically. In a preferred embodiment, a compound of the invention is administered concurrently with the administration of another therapeutic agent. In another preferred embodiment, a composition comprising a compound of the invention is administered concurrently with the administration of another therapeutic agent, which can be part of the same composition as the compound of the invention or a different composition. In another embodiment, a composition comprising a compound of the invention is administered prior or subsequent to administration of another therapeutic agent. Other therapeutic agents, which may be used with the compounds and/or compositions of the invention, include but are not limited to, agonists and antagonists of Edg-3 or other Edg-3 receptors, drugs used to treat cardiovascular diseases and/or cancer such as, alkylating agents (e.g., cyclophosphamide, melphalan, chlorambucil), platinum compounds (e.g., cisplatin, carboplatin), anthracyclines (e.g., doxorubicin, epirubicin), taxanes (e.g., paclitaxel, docetaxel), chronic oral etoposide, topotecan, gemcitabine, hexamethylamine, methotrexate, and 5-fluorouracil.

5.9. Assays

One of skill in the art can use the following assays, for example, to routinely identify and test Edg-3 agonists or antagonists, including Edg-3 selective agonists and antagonists.

5.9.1. Intracellular Calcium Measurement Assays

Specific assays for Edg-3 receptor activity are known to those of skill in the art. For example, cells expressing Edg-3 receptors can be contacted with a membrane-permeant calcium sensitive dye such as Fluo-4 AM or a proprietary calcium dye loading kit (e.g., FLIPR Calcium Assay kit, Molecular Devices, Sunnyvale, Calif.). Intracellular calcium is capable of binding to the dye and emitting fluorescent radiation when illuminated at the appropriate wavelength. The cells can thus be illuminated an appropriate wavelength for the dye and any emitting light can be captured by a cooled CCD camera. Changes in fluorescence indicate changes in intracellular calcium resulting from the activation of an Edg-3 receptor. Such changes can be measured advantageously in whole cells in "real-time" (Berridge et al., Nature Reviews 2000, 1:11–21).

Other methods of measuring intracellular calcium are known to those of skill in the art. For instance, a commonly used technique is the expression of receptors of interest in *Xenopus laevis* oocytes followed by measurement of calcium activated chloride currents (see Weber, 1999, *Biochim Biophys Acta* 1421:213–233). In addition, several calcium sensitive dyes are available for the measurement of intracellular calcium. Such dyes can be membrane permeant or not membrane permeant. Examples of useful membrane permeant dyes include acetoxymethyl ester forms of dyes that can be cleaved by intracellular esterases to form a free acid, which is no longer membrane permeant and remains trapped inside a cell. Dyes that are not membrane permeant can be introduced into the cell by microinjection, chemical permeabilization, scrape loading and similar techniques (Haughland, 1993, in "Fluorescent and Luminescent Probes for Biological Activity" ed. Mason, W. T. pp 34–43; Academic Press, London; Haughland, 1996, in "Handbook of Fluorescent Probes and Research Chemicals", sixth edition, Molecular Probes, Eugene, Oreg.).

5.9.2. IL-8 and VEGF Assays

The levels of interleukin-8 ("IL-8") and vascular endothelial growth factor ("VEGF") are important markers for the proliferative potential, angiogenic capacity and metastatic potential of a tumor cell line. Specific assays for IL-8 and VEGF are known to those of skill in the art. For example, IL-8 and VEGF assays can be performed by techniques that include, but are not limited to, a standard enzyme-linked immunosorbent assay ("ELISA"). In a standard ELISA, the cells can be cultured, for example, in a 96 well format, serum starved overnight, and treated with LPA or S1P. Dose ranges would be known to one of skill in the art. For example, the doses can range from 0.1–10 μM in serum free medium. Cell supernatants can then be collected to measure the amount of IL-8 or VEGF secreted.

Methods to measure the amount of IL-8 or VEGF secreted are known to one of skill in the art. In one method, an anti-IL-8 or anti-VEGF capture antibody can be adsorbed on to any surface, for example, a plastic dish. Cell supernatants containing IL-8 or VEGF can then be added to the dish and any method known in the art for detecting antibodies can be used to detect the anti-IL-8 or anti-VEGF antibody. In one embodiment, an anti-IL-8 or anti-VEGF biotinylated detection antibody and streptavidin-HRP can be used for detection via the addition of a substrate solution and colorimetric reading using a microtiter plate reader. The level of IL-8 or VEGF can be interpolated by non-linear regression analysis from a standard curve.

5.9.3. Migration and Invasion Assays

Migration and invasion assays are known to one of skill in the art. For example, migration assays can be designed to measure the chemotactic potential of the cell line, or its movement toward a concentration gradient of chemoattractants, such as, but not limited to, LPA or S1P. Invasion assays can be designed, for example, to evaluate the ability of the cell line to pass through a basement membrane, a key feature of metastasis formation.

Specific assays, known to one of skill in the art include a modified Boyden Chamber assay in which a cell suspension can be prepared in serum free medium and added to the top chamber. The concentration of cells to be added, for example, about $10^5$ cells/ml is known to one of skill in the art. An appropriate dose of a chemoattractant can then be added to the bottom chamber. Following an incubation period, the number of cells invading the lower chamber can be quantified by methods known in the art. In one embodiment, Fluoroblok filter inserts can be used and the number of cells migrating to the lower chamber can be quantified by staining the filter inserts and detecting the fluorescence by any means known in the art. The level of fluorescence may be correlated with the number of migrating cells.

5.9.4. Proliferation Assay

Proliferation assays quantitate the extent of cellular proliferation in response to a stimulant, which, in the case of Edg-3 receptors, may be S1P. Cells can be plated and treated with the stimulant (e.g., S1P) with or without any serum starvation. Stimulant doses may range from 0.1 to 10 μM and in any event may be readily determined by those of skill in the art. Typically, the cells can be treated for a period of a few hours to a few days before cellular proliferation is measured.

Specific methods to determine the extent of cell proliferation are known to one of skill in the art. For example, one method is bioluminescent measurement of ATP, which is present in all metabolically active cells. ATP can be extracted by addition of Nucleotide Releasing Reagent and its release can be monitored by the addition of the ATP Monitoring Reagent. An enzyme, such as luciferase, which catalyzes the formation of light from ATP and luciferin, can be used to quantitate the amount of ATP present.

5.9.5. Cyclic AMP Assay

Because cAMP acts a second messenger in cell signaling, activating protein kinases that in turn phosphorylate enzymes and transcription factors, cAMP concentration is frequently indicative of the activation state of downstream signaling pathways. For GPCRs like the Edg receptors, coupling via a Gαi pathway results in inhibition of adenylyl cyclase activity, the key enzyme involved in breakdown of ATP and formation of cAMP. Thus, assays can be designed to measure inhibition of adenylyl cyclase activity, by first stimulating cAMP formation. One example of a compound, which stimulates cAMP formation is forskolin. Forskolin bypasses the receptor and directly activates adenylyl cyclase. Under these conditions, activation of a Gαi coupled receptor will inhibit forskolin-stimulated cAMP, and an antagonist at such a receptor will reverse the inhibition.

This assay can be performed by any means known to one of skill in the art. For example, cells can be plated and treated with or without any serum starvation. The cells may be initially treated with a compound, such as forskolin, to induce cAMP production. This is followed by the addition of an Edg-3 stimulator, for example, S1P. The dose of stimulator required is well known in the art, and could be in the range from 0.1–10 μM in serum free medium. Following an incubation period, the cells are lysed and the level of cAMP is determined.

The cAMP assay can be performed by any means known to one of skill in the art, for example, by performing a competitive immunoassay. Cell lysates can be added to a plate precoated with anti-cAMP antibody, along with a cAMP-AP conjugate and a secondary anti-cAMP antibody. Detection can be performed by any appropriate means, including, but not limited to, using a substrate solution and chemiluminescent readout.

6. EXAMPLES

The invention is further defined by reference to the following examples, which describe in detail preparation of compounds and compositions of the invention and assays for using compounds and compositions of the invention. It will be apparent to those skilled in the art that many modifications, both to materials and methods, may be practiced without departing from the scope of the invention.

6.1. Example 1

Synthesis of
3-methyl-2-phenyl-quinoline-4-carboxylic acid
4-fluoro-benzylamide (Compound 101)

3-Methyl-2-phenylquinoline-4-carboxylic acid was prepared by a Pfitzinger reaction (J. Org. Chem. 1950, 15:511–516). Propiophenone (3.3 mL, 1.2 equiv.) was added to a solution of isatin (3.00 g, 20.0 mmol) in ethanol (95%, 30 mL), followed by the addition of KOH pellets (86%, 3.91 g, 3 equiv.). The light brown mixture was stirred at 80° C. (oil bath temperature) for 40 hours. Solvent was removed in vacuo and the resulting solid residue was dissolved in water (50 mL), extracted with ether (30 mL×2) to remove any un-reacted starting materials. The aqueous layer was then cooled with an ice bath and acidified with concentrated aqueous HCl until pH~3. The white precipitate was collected by suction filtration, washed with water and dried in a vacuum oven (30° C.) overnight. The white solid was essentially pure carboxylic acid (5.10 g, 97% yield) and was used for the next step without further purification. $^1$H NMR (300 MHz, DMSO-d6) δ 7.50–8.08 (m, 9H), 2.46 (s, 3H).

3-Methyl-2-phenylquinoline-4-carboxylic acid (1.00 g, 3.80 mmol) was then dissolved in dry THF/CH$_3$CN (70 mL/30 mL). 1-Hydroxy-7-azabenzotriazole (1.31 g, 9.60 mmol, 2.5 equiv), 4-fluorobenzylamine (0.67 mL, 5.85 mmol, 1.50 equiv) were then added and the mixture was cooled in an ice bath. EDC.HCl (1.15 g, 5.99 mmol, 1.58 equiv.) was added in one portion. The ice bath was removed 15 minutes later and the reaction mixture was stirred at room temperature overnight. Organic solvents were removed in vacuo, the residue was taken up in dichloromethane (240 mL), washed with water (60 mL×2) and brine (150 mL), dried with Na$_2$SO$_4$ and evaporated. Flash column chromatography over silica gel (ethyl acetate/dichloromethane (1:20, 1:10)) gave 101 as a white crystalline solid (1.15 g, 82% yield). $^1$H NMR (300 MHz, CDCl$_3$) δ 8.12 (m, 1H), 7.77 (m, 1H), 7.69 (m, 1H), 7.39–7.58 (m, 8H), 7.08 (m, 2H), 6.20 (m, 1H), 4.76 (m, 2H), 2.41 (s, 3H). APCI-MS: m/z 371 [C$_{24}$H$_{19}$FN20+H]$^+$. M.P. 190–191° C.

6.2. Example 2

Alternate Synthesis of Compound 101

2-chlorobenzenesulfonyl isocyanate (0.13 mL, 0.89 mmol) was added to a solution of ethyl 2-amino-4,5,6,7-tetrahydrobenzo[B]thiophene-3-carboxylate (0.20 g, 0.89 mmol) in benzene (2 mL) at room temperature. After 2.5 hours, the reaction mixture was filtered to provide 310 mg (79%) of 101 as a white solid. $^1$H NMR (300 MHz, CDCl$_3$) δ: 11.68 (s, 1H), 8.33 (m, 1H), 7.92 (br s, 1H), 7.57 (m, 2H), 7.43 (m, 1H), 4.39 (m, 2H), 2.73 (m, 2H), 2.58 (m, 2H), 1.75 (m, 4H), 1.38 (m, 3H). CI-MS: m/z=443 [C$_{18}$H$_{19}$ClN$_2$O$_5$S$_2$+H]. Melting Range: 222–225° C.

6.3. Example 3

Selective Inhibition of the Edg-3 Receptor by Compound 101

101 is representative of a series of compounds that demonstrate inhibition of Edg-3 stimulated S1P responses. The compounds were tested in HTC cells expressing human Edg-3 receptors, as well as in NIH 3T3 cell lines that naturally express Edg-3 receptors. The rat hepatoma cell line, HTC, does not express any detectable levels of any of the known Edg receptors. Therefore, HTC proved to be a useful system because Edg 3 could be tested in isolation when recombinantly introduced into these cells. The compounds were tested in this recombinant system first, and subsequently tested in cell lines expressing Edg-3 (in addition to other Edg receptors).

FIG. 1 demonstrates that 101 specifically inhibited Edg-3 receptors. 101 did not inhibit LPA-stimulated calcium increases in HTC cells expressing Edg-2, Edg-4 or Edg-7 receptors and also did not inhibit S1P-stimulated calcium increases in HTC cells expressing Edg-1, Edg-5, Edg-6, or Edg-8 in concentrations as high as 20 □M.

Selectivity of 101 for Edg-3 is also demonstrated in Tables 1 and 2. 101 did not demonstrate any significant activity at various targets tested, including other Edg receptors, GPCRs, and ion channels. Table 1 demonstrates the selectivity of 101 for Edg-3 relative to other Edg receptors. Table 2 is a list of targets, including GPCRs and ion channels, against which 101 (10 μM) showed no activity in standard binding assays. The radioligand binding assays were conducted as described in Section 6.9 (Example 9).

6.4. Example 4

Intracellular Calcium Measurement Assays

LPA receptors such as Edg-3, couple to calcium effector pathways, and result in increases in intracellular calcium following receptor activation (An, 1998, J. Cell Biochem. Supp 30–31:147–157). This biological response lends itself to a very efficient, high-throughput screen using a Fluorescence Imaging Plate Reader (FLIPR; Molecular Devices, Sunnyvale, Calif.). The FLIPR system is a real-time, cell-based assay system with continuous fluorescence detection using a cooled CCD camera. The FLIPR system was used to developing an Edg-3 receptor screen. Rat hepatoma cells stably expressing Edg-3 receptor were plated on 384-well plates and loaded with a calcium dye loading kit (Molecular Devices, Sunnyvale, Calif.) for 1 hour at room temperature. Cells were then placed on the FLIPR$^{384}$ (Molecular Devices, Sunnyvale, Calif.) and excited by an argon laser at 488 nm. The data for the entire 384-well plate was updated every second. An integrated robotic pipettor allowed for simultaneous compound addition into each individual well in the plate.

6.5. Example 5

IL-8 and VEGF Assays

IL-8 and VEGF assays were performed by standard enzyme-linked immunosorbent assay ("ELISA") techniques. Cells were cultured in a 96 well format, serum starved overnight, and treated with LPA or S1P (doses range from 0.1–10 µM in serum free medium) for 24 hours. Cell supernatants were then collected to measure the amount of IL-8 secreted.

The assay was a standard sandwich ELISA in which an anti-IL-8 or VEGF capture antibody was adsorbed to a plastic dish. Cell supernatants containing IL-8 or VEGF were added to the dish, and then an anti-IL-8/VEGF biotinylated detection antibody and streptavidin-HRP were added.

Detection was via the addition of a substrate solution and colorimetric reading using a microtiter plate reader. The level of IL-8 or VEGF was interpolated by non-linear regression analysis from a standard curve.

All reagents were from R&D Systems, Minneapolis, Minn.: MAB208 and AF-293-NA (capture antibody for IL-8 and VEGF respectively), BAF208 and BAF-293 (detection Ab for IL-8 and VEGF respectively), 208-IL-010 and 293-VE-010 (recombinant human IL-8 protein standard and recombinant human VEGF protein standard respectively), DY998 (streptavidin-HRP), DY999 (substrate solution).

6.6. Example 6

Migration and Invasion Assays

Cells were plated in a 24 well format using Fluoroblok filter insert plates (8 µM pore size) or Fluoroblok matrigel coated filter insert plates (Becton Dickinson, San Diego, Calif., Catalog # 351158, 354166, respectively). The assay was a modified Boyden Chamber assay in which a cell suspension ($1 \times 10^5$ cells/ml) was prepared in serum free medium and added to the top chamber. LPA or SP1 (doses ranged from 0.1–10 µM in serum free medium) was added to the bottom chamber. Following a 20–24 hour incubation period, the number of cells migrating or invading into the lower chamber was quantitated by transferring the filter insert into a fresh 24-well plate containing 4 µg/ml calcein AM (Molecular Probes, Sunnyvale, Calif., Catalog #C-1430) in Hank's Balanced Salt Solution and staining for one hour.

Detection was via fluorescent readout at 450 nm excitation/530 nm emission using the BioTek FLx800 Fluorimeter. The level of fluorescence correlated with cell number.

For most cells types, no further manipulation was required. For CaOV3 human ovarian cancer cells, however, it was necessary that the cells be serum starved overnight prior to preparing the cell suspension. In addition, the filter inserts were coated with a solution of 1 mg/ml rat-tail Collagen I (BD, SanDiego, Calif., Catalog # 354236).

6.7. Example 7

Proliferation Assay

Cells were plated in a 96 well format. Treatments were performed directly without any serum starvation, and typically included LPA or S1P doses in a range from 0.1–10 µM in serum free medium. Cells were treated for 24–48 before the extent of cellular proliferation was measured.

The assay was performed using the ViaLight HS kit (BioWhittaker, Rockland, Me., Catalog # LT07-211) which is based upon the bioluminescent measurement of ATP that is present in all metabolically active cells. The reaction utilized an enzyme, luciferase, which catalyzes the formation of light from ATP and luciferin. The emitted light intensity was linearly related to the ATP concentration, which correlated with cell number.

Measurement of cell proliferation required the extraction of ATP by the addition of Nucleotide Releasing Reagent, followed by the addition of the ATP Monitoring Reagent (both provided in kit). Detection was via chemiluminescence using the EG&G Berthold Luminometer, Gaithersburg, Md.

6.8. Example 8 cAMP Assay

Cells were plated in a 96 well format. Treatments were performed directly without any serum starvation. The cells were treated with forskolin to induce cAMP production, followed by LPA or S1P doses in the range from 0.1–10 µM in serum free medium. Following a 30-minute incubation period, the cells were lysed and the level of cAMP was determined.

The cAMP assay was performed using the Tropix cAMP-Screen (Applied BioSystems, Foster City, Calif., Catalog # CS1000). The screen is a competitive immunoassay that utilizes a 96 well assay plate precoated with an anti-cAMP antibody. Cell lysates were added to the precoated plate, along with a cAMP-AP conjugate and a secondary anti-cAMP antibody.

Detection was performed using a substrate solution and chemiluminescent readout. The level of chemiluminescence was inversely proportional to the level of cAMP and was calculated from a standard curve.

6.9. Example 9

Pharmacology Profiling (Selectivity Assays)

In order to test the selectivity of compounds, various enzyme assays as well as radioligand binding assays were performed using numerous non-Edg receptor targets as listed below.

A radioligand binding assay was performed using adrenergic $\alpha_1$ according to the method of Greengrass and Bremner 1979, *Eur. J. Pharmacol.* 55:323–326. A radioligand binding assay was performed using adrenergic $\alpha_2$ according to the method of Boyajian and Leslie, 1987, *J. Pharmacol. Exp. Ther.* 241:1092–1098. A radioligand binding assay was performed using adrenergic β according to the method of Feve et al., 1994, *Proc. Natl. Acad. Sci. USA* 91:5677–5681. A radioligand binding assay was performed using angiotensin AT2 according to the method of Whitebread et al., 1991, *Biochem. Biophys. Res. Comm.* 181:1365–1371. A radioligand binding assay was performed using calcium channel Type L, dihydropyridine according to the method of Ehlert et al., 1982, *Life Sci.* 30:2191–2202. A radioligand binding assay was performed using dopamine $D_{2L}$ according to the method of Bunzo et al., 1988, *Nature* 336:783–787. A radioligand binding assay was performed using endothelin $ET_A$ according to the method of Mihara et al., 1994, *J. Phrmacol. Exp Ther.* 268:1122–1127. A radioligand binding assay was performed using histamine $H_1$ Central according to the method of Hill et al., 1978, *J. Neurochem.* 31:997–1004. A radioligand binding assay was performed using Muscarinic non-selective, Central according to the method of Luthin and Wolfe, 1984, *J. Pharmacol. Exp. Ther.* 228:648–655. A radioligand binding assay was performed using serotonin 5-HT1, non-selective according to the method of Middlemiss, 1984, *Eur. J. Pharmacol.* 101: 289–293).

Radioligand Binding assays

1. Adrenergic $\alpha_1$, non-selective (Broadhurst et al., 1988, *Life Sci.* 43:83–92).
   Source: Wistar Rat brain
   Ligand: 0.25 nM $^3H$ Prazosin
   Vehicle: 0.4% DMSO
   Incubation Time/Temp: 30 minutes at 25° C.
   Incubation Buffer: 50 mM Tris-HCl, 0.1% ascorbic acid, 10 uM
   NonSpecific Ligand: 0.1 µM Phentolamine
   $K_d$: 0.29 nM*
   $B_{max}$: 0.095 pmol/mg Protein*
   Specific Binding: 90%*
   Quantitation Method: Radioligand Binding
   Significance Criteria: ≧50% of max stimulation or inhibition 2. Adrenergic $\alpha_2$ (Boyajian and Leslie, 1987, *J. Pharmacol. Exp. Ther.* 241:1092–1098).
   Source: Wistar rat cerebral cortex
   Ligand: 0.7 nM $^3H$ Rauwolscine
   Vehicle: 0.4% DMSO
   Incubation Time/Temp: 30 minutes at 25° C.
   Incubation Buffer: 20 mM HEPES, 2.5 mM Tris-HCl, pH 7.4 at 25° C.
   NonSpecific Ligand: 1 µM Yohimbine
   $K_d$: 7.8 nM*
   $B_{max}$: 0.36 pmol/mg Protein*
   Specific Binding: 80%*
   Quantitation Method: Radioligand Binding
   Significance Criteria: ≧50% of max stimulation or inhibition 3. Adrenergic β (Feve et al., 1994, *Proc. Natl. Acad. Sci. USA* 91:5677–5681).
   Source: Wistar rat brain
   Ligand: 0.25 nM $^3H$ Dihydroaplenolol
   Vehicle: 0.4% DMSO
   Incubation Time/Temp: 20 minutes at 25° C.
   Incubation Buffer: 50 mM Tris-HCl, pH 7.4
   NonSpecific Ligand: 1 µM S(-)-Propranolol
   $K_d$: 0.5 nM*
   $B_{max}$: 0.083 pmol/mg Protein*
   Specific Binding: 85%*
   Quantitation Method: Radioligand Binding
   Significance Criteria: ≧50% of max stimulation or inhibition 4. Angiotensin AT2 (Whitebread et al., 1991, *Biochem. Biophys. Res. Comm.* 181:1365–1371).
   Source: Human recombinant Hela cells
   Ligand: 0.025 nM 125I CGP-42112A
   Vehicle: 0.4% DMSO
   Incubation Time/Temp: 3 hours at 37° C.
   Incubation Buffer: 50 mM Tris-HCl, 5 mM $MgCl_2$, 0.1% BSA, 1 mM EDTA, pH 7.4
   NonSpecific Ligand: 10 µM [$Sar^1$, $Ile^8$]-Ang II
   $K_d$: 0.012 nM*
   $B_{max}$: 2.9 pmol/mg Protein*
   Specific Binding: 90%*
   Quantitation Method: Radioligand Binding
   Significance Criteria: ≧50% of max stimulation or inhibition 5. Calcium Channel Type L, Dihydropyridine (Ehlert et al., 1982, *Life Sci.* 30:2191–2202).
   Source: Wistar Rat cerebral cortex
   Ligand: 0.1 nM $^3H$ Nitrendipine
   Vehicle: 0.4% DMSO
   Incubation Time/Temp: 90 minutes at 25° C.
   Incubation Buffer: 50 mM Tris-HCl, pH 7.7
   NonSpecific Ligand: 1 µM Nitrendipine
   $K_d$: 0.18 nM*
   $B_{max}$: 0.23 pmol/mg Protein*
   Specific Binding: 91%*
   Quantitation Method: Radioligand Binding
   Significance Criteria: ≧50% of max stimulation or inhibition 6. Dopamine $D_{2L}$ (Bunzo et al., 1988, *Nature* 336:783–787).
   Source: Human recombinant CHO cells
   Ligand: 0.16 nM $^3H$ Spiperone
   Vehicle: 0.4% DMSO
   Incubation Time/Temp: 2 hours at 25° C.
   Incubation Buffer: 50 mM Tris-HCl, pH 7.4, 150 mM NaCl, 1.4 mM ascorbic acid, 0.001% BSA
   NonSpecific Ligand: 10 µM Haloperidol
   $K_d$: 0.08 nM*
   $B_{max}$: 0.48 pmol/mg Protein*
   Specific Binding: 85%*
   Quantitation Method: Radioligand Binding
   Significance Criteria: ≧50% of max stimulation or inhibition 7. Endothelin $ET_A$ (Mihara et al., 1994, *J. Phrmacol. Exp Ther.* 268:1122–1127).
   Source: Human recombinant CHO cells
   Ligand: 0.03 nM $^{125}I$ Endothelin
   Vehicle: 0.4% DMSO
   Incubation Time/Temp: 2 hours at 37° C.
   Incubation Buffer: 50 mM Tris-HCl, pH 7.4, 0.5 mM CaCl2, 0.1% bacitracin, 0.05% Tween-20, 1 mg/ml BSA
   NonSpecific Ligand: 0.1 µM Endothelin 1
   $K_d$: 0.048 nM*
   $B_{max}$: 0.35 pmol/mg Protein*
   Specific Binding: 90%*
   Quantitation Method: Radioligand Binding
   Significance Criteria: ≧50% of max stimulation or inhibition 8. Histamine $H_1$, Central (Hill et al., 1978, *J. Neurochem.* 31:997–1004).
   Source: Guinea pig cerebellum
   Ligand: 1.75 nM $^3H$ Pyrilamine
   Vehicle: 0.4% DMSO
   Incubation Time/Temp: 60 minutes at 25° C.
   Incubation Buffer: 50 mM K-Na phosphate buffer pH 7.4 at 25° C.
   NonSpecific Ligand: 1 µM Pyrilamine
   $K_d$: 0.23 nM*
   $B_{max}$: 0.198 pmol/mg Protein*
   Specific Binding: 90%*
   Quantitation Method: Radioligand Binding Significance Criteria: ≧50% of max stimulation or inhibition 9. Muscarinic non-selective, Central (Luthin and Wolfe, 1984, *J. Pharmacol. Exp. Ther.* 228:648–655).
Source: Wistar rat cerebral cortex
Ligand: 0.29 nM $^3$H Quinuclidinyl benzilate
Vehicle: 0.4% DMSO
Incubation Time/Temp: 60 minutes at 25° C.
Incubation Buffer: 50 mM Na-K Phosphate, pH 7.4
NonSpecific Ligand: 0.1 µM Atropine
$K_d$: 0.068 nM*
$B_{max}$: 1.4 pmol/mg Protein*
Specific Binding: 97%*
Quantitation Method: Radioligand Binding
Significance Criteria: ≧50% of max stimulation or inhibition 10. Serotonin 5-HT1, non-selective (Middlemiss, 1984, *Eur. J. Pharmacol.* 101:289–293).
Source: Wistar rat cerebral cortex
Ligand: 2 nM $^3$H Serotonin (5-HT) Trifluoroacetate
Vehicle: 0.4% DMSO
Incubation Time/Temp: 10 minutes at 25° C.
Incubation Buffer: 50 mM Tris-HCl, 0.1% ascorbic acid, 10 µM pargyline, 4 mM CaC12, pH 7.6
NonSpecific Ligand: 10 µM 5-HT (Serotonin)
$K_d$: 0.61 nM*
$B_{max}$: 0.58 pmol/mg Protein*
Specific Binding: 80%*
Quantitation Method: Radioligand Binding
Significance Criteria: ≧50% of max stimulation or inhibition
* Historical Values Finally, it should be noted that there are alternative ways of implementing both the present invention. Accordingly, the present embodiments are to be considered as illustrative and not restrictive, and the invention is not to be limited to the details given herein, but may be modified within the scope and equivalents of the appended claims.

All publications and patents cited herein incorporated by reference in their entirety.

What is claimed is:

1. A method of modulating an Edg-3 receptor mediated biological activity comprising contacting a cell expressing the Edg-3 receptor with an amount of a non-phospholipid modulator of the Edg-3 receptor sufficient to modulate the Edg-3 receptor mediated biological activity, wherein the modulator is a compound of Formula (VI):

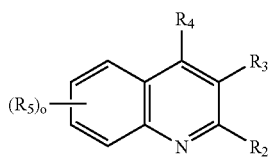

or a pharmaceutically acceptable solvate or hydrate thereof, wherein
  o is a member selected from the integers 0 to 4;
  each $R_2$ and $R_4$ is a member independently selected from the group consisting of hydrogen, alkyl, substituted alkyl, acyl, substituted acyl, acylamino, substituted acylamino, alkylamino, substituted alkylamino, alkylthio, substituted alkylthio, alkoxy, substituted alkoxy, alkoxycarbonyl, substituted alkoxycarbonyl, alkylarylamino, substituted alkylarylamino, arylalkyloxy, substituted arylalkyloxy, amino, aryl, substituted aryl, arylalkyl, substituted arylalkyl, arylamino, substituted arylamino, arylsulfonyl, substituted arylsulfonyl, carboxy, carbamoyl, substituted carbamoyl, cycloalkyl, substituted cycloalkyl, cycloheteroalkyl, substituted cycloheteroalkyl, dialkylamino, substituted dialkylamino, heteroaryloxy, substituted heteroaryloxy, heteroaryl, substituted heteroaryl, heteroalkyl, and substituted heteroalkyl; and
  $R_3$ is a member independently selected from the group consisting of alkyl, substituted alkyl, acyl, substituted acyl, acylamino, substituted acylamino, alkylamino, substituted alkylamino, alkoxycarbonyl, substituted alkoxycarbonyl, alkylarylamino, substituted alkylarylamino, aryl, substituted aryl, arylalkyl, substituted arylalkyl, arylamino, substituted arylamino, carbamoyl, substituted carbamoyl, dialkylamino, substituted dialkylamino, heteroaryl, substituted heteroaryl, heteroalkyl, and substituted heteroalkyl; and
  each $R_5$ is a member independently selected from the group consisting of alkyl, acyl, substituted acyl, acylamino, substituted acylamino, alkylamino, substituted alkylamino, alkylarylamino, substituted alkylarylamino, amino, aryl, substituted aryl, arylalkyl, substituted arylalkyl, arylsulfonyl, substituted arylsulfonyl, azido, carboxy, carbamoyl, substituted carbamoyl, carboxyl, cyano, cycloalkyl, substituted cycloalkyl, cycloheteroalkyl, substituted cycloheteroalkyl, dialkylamino, substituted dialkylamino, halo, heteroaryl, substituted heteroaryl, hydroxyl, and nitro.

2. A method of modulating an Edg-3 receptor mediated biological activity in a subject comprising administering to the subject a therapeutically effective amount of a non-phospholipid modulator of the Edg-3 receptor, wherein the modulator is a compound of Formula (VI):

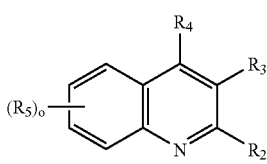

or a pharmaceutically acceptable solvate or hydrate thereof, wherein
  o is a member selected from the integers 0 to 4;
  each $R_2$ and $R_4$ is a member independently selected from the group consisting of hydrogen, alkyl, substituted alkyl, acyl, substituted acyl, acylamino, substituted acylamino, alkylamino, substituted alkylamino, alkylthio, substituted alkylthio, alkoxy, substituted alkoxy, alkoxycarbonyl, substituted alkoxycarbonyl, alkylarylamino, substituted alkylarylamino, arylalkyloxy, substituted arylalkyloxy, amino, aryl, substituted aryl, arylalkyl, substituted arylalkyl, arylamino, substituted arylamino, arylsulfonyl, substituted arylsulfonyl, carboxy, carbamoyl, substituted carbamoyl, cycloalkyl, substituted cycloalkyl, cycloheteroalkyl, substituted cycloheteroalkyl, dialkylamino, substituted dialkylamino, heteroaryloxy, substituted heteroaryloxy, heteroaryl, substituted heteroaryl, heteroalkyl, and substituted heteroalkyl;
  $R_3$ is a member independently selected from the group consisting of alkyl, substituted alkyl, acyl, substituted acyl, acylamino, substituted acylamino, alkylamino, substituted alkylamino, alkoxycarbonyl, substituted alkoxycarbonyl, alkylarylamino, substituted alkylarylamino, aryl, substituted aryl, arylalkyl, substituted arylalkyl, arylamino, substituted arylamino, carbamoyl, substituted carbamoyl, dialkylamino, substituted dialkylamino, heteroaryl, substituted heteroaryl, heteroalkyl, and substituted heteroalkyl; and each R$_5$ is a member independently selected from the group consisting of alkyl, acyl, substituted acyl, acylamino, substituted acylamino, alkylamino, substituted alkylamino, alkylarylamino, substituted alkylarylamino, amino, aryl, substituted aryl, arylalkyl, substituted arylalkyl, arylsulfonyl, substituted arylsulfonyl, azido, carboxy, carbamoyl, substituted carbamoyl, carboxyl, cyano, cycloalkyl, substituted cycloalkyl, cycloheteroalkyl, substituted cycloheteroalkyl, dialkylamino, substituted dialkylamino, halo, heteroaryl, substituted heteroaryl, hydroxyl, and nitro.

3. The method of claim 1 or 2, wherein the modulator is an antagonist.

4. The method of claim 1 or 2, wherein the modulator exhibits at least about 200 fold inhibitory selectivity for Edg-3 relative to Edg 2, Edg-4 and Edg-7 receptors.

5. The method of claim 1 or 2, wherein the modulator exhibits at least about 100 fold inhibitory selectivity for Edg-3 relative to Edg 2, Edg-4 and Edg-7 receptors.

6. The method of claim 1 or 2, wherein the modulator exhibits at least about 20 fold inhibitory selectivity for Edg-3 relative to Edg 2, Edg-4 and Edg-7 receptors.

7. The method of claim 1 or 2, wherein the modulator exhibits at least about 5 fold inhibitory selectivity for Edg-3 relative to Edg 2 Edg-4 and Edg-7 receptors.

8. The method of claim 1 or 2, wherein the modulator exhibits at least about 200 fold inhibitory selectivity for Edg-3 relative to Edg-1, Edg-5, Edg-6 and Edg-8 receptors.

9. The method of claim 1 or 2, wherein the modulator exhibits at least about 100 fold inhibitory selectivity for Edg-3 relative to Edg-1, Edg-5, Edg-6 and Edg-8 receptors.

10. The method of claim 1 or 2, wherein the modulator exhibits at least about 20 fold inhibitory selectivity for Edg-3 relative to Edg-1, Edg-5, Edg-6 and Edg-8 receptors.

11. The method of claim 1 or 2, wherein the modulator exhibits at least about 5 fold inhibitory selectivity for Edg-3 relative to Edg-1, Edg-5, Edg-6 and Edg-8 receptors.

12. The method of claim 1 or 2, wherein the biological activity is cell proliferation.

13. The method of claim 12, wherein cell proliferation leads to cancer selected from the group consisting of ovarian cancer, peritoneal cancer, endometrial cancer, cervical cancer, breast cancer, colon cancer and prostate cancer.

14. The method of claim 12, wherein cell proliferation is stimulated by S1P.

15. The method of claim 1 or 2, wherein the biological activity is a member selected from the group consisting of calcium mobilization, VEGF synthesis, IL-8 synthesis, platelet activation, cell migration, phosphoinositide hydrolysis, inhibition of cAMP formation, increasing the level of fatty acids, actin polymerization, apoptosis, angiogenesis, inhibition of wound healing, inflammation, expression of endogenous protein growth factors, cancer invasiveness, vasoconstriction and atherogenesis.

16. The method of claim 1 or 2 wherein the modulator binds to the Edg-3 receptor with a binding constant between about 1 fM to about 10 μM.

17. The method of claim 1 or 2 wherein the modulator binds to the Edg-3 receptor with a binding constant of at least about 1 μM.

18. The method of claim 1 or 2 wherein the modulator binds to the Edg-3 receptor with a binding constant of at least about 10 nM.

19. The method of claim 1 or 2, wherein the modulator is an organic molecule of molecular weight of less than 750 daltons.

20. The method of claim 1, wherein the cell is a member selected from the group consisting of a HTC hepatoma cell, an ovarian cell, an epithelial cell, a fibroblast cell, a neuronal cell, a carcinoma cell, a pheochromocytoma cell, a myoblast cell, a platelet cell and a fibrosarcoma cell.

21. The method of claim 16, wherein the cell is a member selected from the group consisting of OV202 human ovarian cell, a HTC rat hepatoma cell, a CAOV-3 human ovarian cancer cell, MDA-MB-453 breast cancer cell, MDA-MB-231 breast cancer cell, HUVEC cells A431 human epitheloid carcinoma cell and a HT-1080 human fibrosarcoma cell.

22. The method of claim 1 or 2, wherein the modulator is a compound of the formula:

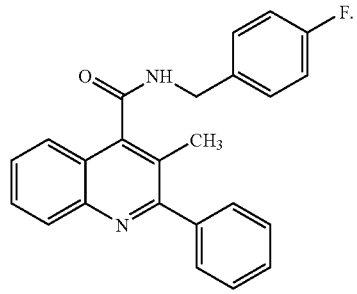

101

23. A method for treating of cardiovascular diseases in a patient in need of such treatment, said method comprising administering to said patient a therapeutically effective amount of a compound of Formula (VI), wherein said compound of Formula (VI) is:

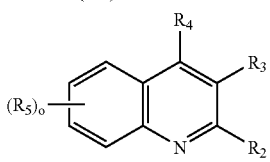

(VI)

or a pharmaceutically acceptable solvate or hydrate thereof, wherein o is a member selected from the integers 0 to 4;

each R$_2$ and R$_4$ is a member independently selected from the group consisting of hydrogen, alkyl, substituted alkyl, acyl, substituted acyl, acylamino, substituted acylamino, alkylamino, substituted alkylamino, alkylthio, substituted alkylthio, alkoxy, substituted alkoxy, alkoxycarbonyl, substituted alkoxycarbonyl, alkylarylamino, substituted alkylarylamino, arylalkyloxy, substituted arylalkyloxy, amino, aryl, substituted aryl, arylalkyl, substituted arylalkyl, arylamino, substituted arylamino, arylsulfonyl, substituted arylsulfonyl, carboxy, carbamoyl, substituted carbamoyl, cycloalkyl, substituted cycloalkyl, cycloheteroalkyl, substituted cycloheteroalkyl, dialkylamino, substituted dialkylamino, heteroaryloxy, substituted heteroaryloxy, heteroaryl, substituted heteroaryl, heteroalkyl, and substituted heteroalkyl; and R$_3$ is a member independently selected from the group consisting of alkyl, substituted alkyl, acyl, substituted acyl, acylamino, substituted acylamino, alkylamino, substituted alkylamino, alkoxycarbonyl, substituted alkoxycarbonyl, alkylarylamino, substituted alkylarylamino, aryl, substituted aryl, arylalkyl, substituted arylalkyl, arylamino, substituted arylamino, carbamoyl, substituted carbamoyl, dialkylamino, substituted dialkylamino, heteroaryl, substituted heteroaryl, heteroalkyl, and substituted heteroalkyl;

each $R_5$ is a member independently selected from the group consisting of alkyl, acyl substituted acyl, acylamino, substituted acylamino, alkylamino, substituted alkylamino, alkylarylamino, substituted alkylarylamino, amino, aryl, substituted aryl, arylalkyl substituted arylalkyl, arylsulfonyl, substituted arylsulfonyl, azido, carboxy carbamoyl, substituted carbamoyl, carboxyl, cyano, cycloalkyl substituted cycloalkyl, cycloheteroalkyl, substituted cycloheteroalkyl, dialkylamino, substituted dialkylamino, halo, heteroaryl, substituted heteroaryl, hydroxyl, and nitro.

24. A method for treating ischemia or atherosclerosis in a patient in need of such treatment, said method comprising administering to said patient a therapeutically effective amount of a compound of Formula (VI), wherein said compound of Formula (VI) is: (VI)

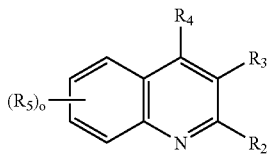

or a pharmaceutically acceptable solvate or hydrate thereof, wherein o is a member selected from the integers 0 to 4;

each $R_2$ and $R_4$ is a member independently selected from the group consisting of hydrogen, alkyl, substituted alkyl, acyl, substituted acyl, acylamino, substituted acylamino, alkylamino, substituted alkylamino, alkylthio, substituted alkylthio, alkoxy, substituted alkoxy, alkoxycarbonyl, substituted alkoxycarbonyl, alkylarylamino, substituted alkylarylamino, arylalkyloxy, substituted arylalkyloxy, amino, aryl, substituted aryl, arylalkyl, substituted arylalkyl, arylamino, substituted arylamino, arylsulfonyl, substituted arylsulfonyl, carboxy, carbamoyl, substituted carbamoyl, cycloalkyl, substituted cycloalkyl, cycloheteroalkyl, substituted cycloheteroalkyl, dialkylamino, substituted dialkylamino, heteroaryloxy, substituted heteroaryloxy, heteroaryl, substituted heteroaryl, heteroalkyl, and substituted heteroalkyl;

$R_3$ is a member independently selected from the group consisting of alkyl, substituted alkyl, acyl, substituted acyl, acylamino, substituted acylamino, alkylamino, substituted alkylamino, alkoxycarbonyl, substituted alkoxycarbonyl, alkylarylamino, substituted alkylarylamino, aryl, substituted aryl, arylalkyl, substituted arylalkyl, arylamino, substituted arylamino, carbamoyl, substituted carbamoyl, dialkylamino, substituted dialkylamino, heteroaryl, substituted heteroaryl, heteroalkyl, and substituted heteroalkyl;

each $R_5$ is a member independently selected from the group consisting of alkyl, acyl, substituted acyl, acylamino, substituted acylamino, alkylamino, substituted alkylamino, alkylarylamino, substituted alkylarylamino, amino, aryl, substituted aryl, arylalkyl, substituted arylalkyl, arylsulfonyl, substituted arylsulfonyl, azido, carboxy, carbamoyl, substituted carbamoyl, carboxyl, cyano, cycloalkyl, substituted cycloalkyl, cycloheteroalkyl, substituted cycloheteroalkyl, dialkylamino, substituted dialkylamino, halo, heteroaryl, substituted heteroaryl, hydroxyl, and nitro.

25. A method for treating vasoconstriction, or vascular occlusive disorders in a patient in need of such treatment, said method comprising administering to said patient a therapeutically effective amount of a compound of Formula (VI), wherein said compound of Formula (VI) is: (VI)

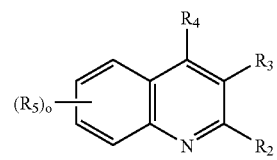

or a pharmaceutically acceptable solvate or hydrate thereof, wherein o is a member selected from the integers 0 to 4;

each $R_2$ and $R_4$ is a member independently selected from the group consisting of hydrogen, alkyl, substituted alkyl, acyl, substituted acyl, acylamino, substituted acylamino, alkylamino, substituted alkylamino, alkylthio, substituted alkylthio, alkoxy, substituted alkoxy, alkoxycarbonyl, substituted alkoxycarbonyl, alkylarylamino, substituted alkylarylamino, arylalkyloxy, substituted arylalkyloxy, amino, aryl, substituted aryl, arylalkyl, substituted arylalkyl, arylamino, substituted arylamino, arylsulfonyl, substituted arylsulfonyl, carboxy, carbamoyl, substituted carbamoyl, cycloalkyl, substituted cycloalkyl, cycloheteroalkyl, substituted cycloheteroalkyl, dialkylamino, substituted dialkylamino, heteroaryloxy, substituted heteroaryloxy, heteroaryl, substituted heteroaryl, heteroalkyl, and substituted heteroalkyl;

$R_3$ is a member independently selected from the group consisting of alkyl, substituted alkyl, acyl, substituted acyl, acylamino, substituted acylamino, alkylamino, substituted alkylamino, alkoxycarbonyl, substituted alkoxycarbonyl, alkylarylamino, substituted alkylarylamino, aryl, substituted aryl, arylalkyl, substituted arylalkyl, arylamino, substituted arylamino, carbamoyl, substituted carbamoyl, dialkylamino, substituted dialkylamino, heteroaryl, substituted heteroaryl, heteroalkyl, and substituted heteroalkyl;

each $R_5$ is a member independently selected from the group consisting of alkyl, acyl, substituted acyl, acylamino, substituted acylamino, alkylamino, substituted alkylamino, alkylarylamino, substituted alkylarylamino, amino, aryl, substituted aryl, arylalkyl, substituted arylalkyl, arylsulfonyl, substituted arylsulfonyl, azido, carboxy, carbamoyl, substituted carbamoyl, carboxyl, cyano, cycloalkyl substituted cycloalkyl, cycloheteroalkyl, substituted cycloheteroalkyl, dialkylamino, substituted dialkylamino, halo, heteroaryl, substituted heteroaryl, hydroxyl, and nitro.

26. A method for treating vasoconstriction in cerebral arteries or vasospasm in a patient, in need of such treatment, said method comprising administering to a said patient a therapeutically effective amount of a compound of Formula (VI), wherein said compound of Formula (VI) is:

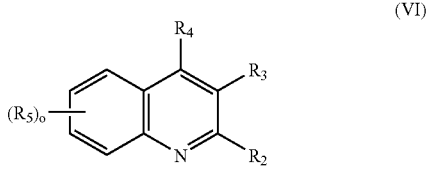

or a pharmaceutically acceptable solvate or hydrate thereof, wherein o is a member selected from the integers 0 to 4;

each $R_2$ and $R_4$ is a member independently selected from the group consisting of hydrogen, alkyl substituted alkyl, acyl, substituted acyl acylamino, substituted acylamino, alkylamino, substituted alkylamino, alkylthio, substituted alkylthio, alkoxy, substituted alkoxy, alkoxycarbonyl, substituted alkoxycarbonyl alkylarylamino, substituted alkylarylamino, arylalkyloxy, substituted arylalkyloxy, amino, aryl, substituted aryl, arylalkyl substituted arylalkyl arylamino, substituted arylamino, arylsulfonyl substituted arylsulfonyl, carboxy, carbamoyl, substituted carbamoyl, cycloalkyl, substituted cycloalkyl, cycloheteroalkyl, substituted cycloheteroalkyl, dialkylamino, substituted dialkylamino, heteroaryloxy, substituted heteroaryloxy heteroaryl, substituted heteroaryl, heteroalkyl, and substituted heteroalkyl;

$R_3$ is a member independently selected from the group consisting of alkyl, substituted alkyl, acyl, substituted acyl, acylamino, substituted acylamino, alkylamino, substituted alkylamino, alkoxycarbonyl, substituted alkoxycarbonyl, alkylarylamino, substituted alkylarylamino, aryl, substituted aryl, arylalkyl, substituted arylalkyl, arylamino, substituted arylamino, carbamoyl, substituted carbamoyl, dialkylamino, substituted dialkylamino, heteroaryl, substituted heteroaryl, heteroalkyl, and substituted heteroalkyl;

each $R_5$ is a member independently selected from the group consisting of alkyl, acyl, substituted acyl, acylamino, substituted acylamino, alkylamino, substituted alkylamino, alkylarylamino, substituted alkylarylamino, amino, aryl, substituted aryl, arylalkyl, substituted arylalkyl, arylsulfonyl, substituted arylsulfonyl, azido, carboxy, carbamoyl, substituted carbamoyl, carboxyl, cyano, cycloalkyl, substituted cycloalkyl, cycloheteroalkyl, substituted cycloheteroalkyl, dialkylamino, substituted dialkylamino, halo, heteroaryl, substituted heteroaryl, hydroxyl, and nitro.

27. A method for treating cardiovascular diseases, vasoconstriction, or vascular occlusive disorders in a patient in need of such treatment, said method comprising administering to said patient a therapeutically effective amount of a compound of Formula (VI), wherein said compound of Formula (VI) is:

(VI)

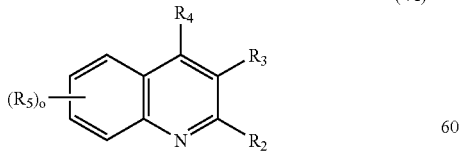

or a pharmaceutically acceptable solvate or hydrate thereof, wherein o is a member selected from the integers 0 to 4;

each $R_2$ and $R_4$ is a member independently selected from the group consisting of hydrogen, alkyl substituted alkyl, acyl, substituted acyl, acylamino, substituted acylamino, alkylamino, substituted alkylamino, alkylthio, substituted alkylthio, alkoxy, substituted alkoxy, alkoxycarbonyl, substituted alkoxycarbonyl, alkylarylamino, substituted alkylarylamino, arylalkyloxy, substituted arylalkyloxy, amino, aryl, substituted aryl, arylalkyl, substituted arylalkyl, arylamino, substituted arylamino, arylsulfonyl, substituted arylsulfonyl, carboxy, carbamoyl, substituted carbamoyl, cycloalkyl, substituted cycloalkyl, cycloheteroalkyl, substituted cycloheteroalkyl, dialkylamino, substituted dialkylamino, heteroaryloxy, substituted heteroaryloxy, heteroaryl, substituted heteroaryl, heteroalkyl, and substituted heteroalkyl;

$R_3$ is a member independently selected from the group consisting of alkyl, substituted alkyl, acyl, substituted acyl, acylamino, substituted acylamino, alkylamino, substituted alkylamino, alkoxycarbonyl, substituted alkoxycarbonyl, alkylarylamino, substituted alkylarylamino, aryl, substituted aryl, arylalkyl, substituted arylalkyl, arylamino, substituted arylamino, carbamoyl, substituted carbamoyl, dialkylamino, substituted dialkylamino, heteroaryl, substituted heteroaryl, heteroalkyl, and substituted heteroalkyl;

each $R_5$ is a member independently selected from the group consisting of alkyl, acyl, substituted acyl, acylamino, substituted acylamino, alkylamino, substituted alkylamino, alkylarylamino, substituted alkylarylamino, amino, aryl, substituted aryl, arylalkyl, substituted arylalkyl, arylsulfonyl, substituted arylsulfonyl, azido, carboxy, carbamoyl, substituted carbamoyl, carboxyl, cyano, cycloalkyl, substituted cycloalkyl, cycloheteroalkyl, substituted cycloheteroalkyl, dialkylamino, substituted dialkylamino, halo, heteroaryl, substituted heteroaryl, hydroxyl, and nitro; and one or more antagonists of an Edg receptor.

28. A method for treating cardiovascular diseases, vasoconstriction or vascular occlusive disorders in a patient, in need of such treatment, said method comprising administering to said patient a therapeutically effective amount of a compound of Formula (VI), wherein said compound of Formula (VI) is:

(VI)

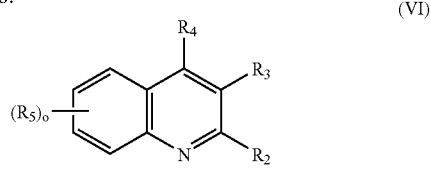

or a pharmaceutically acceptable solvate or hydrate thereof, wherein o is a member selected from the integers 0 to 4;

each $R_2$ and $R_4$ is a member independently selected from the group consisting of hydrogen, alkyl, substituted alkyl, acyl, substituted acyl, acylamino, substituted acylamino, alkylamino, substituted alkylamino, alkylthio, substituted alkylthio, alkoxy, substituted alkoxy, alkoxycarbonyl, substituted alkoxycarbonyl, alkylarylamino, substituted alkylarylamino, arylalkyloxy, substituted arylalkyloxy, amino, aryl, substituted aryl, arylalkyl, substituted arylalkyl, arylamino, substituted arylamino, arylsulfonyl, substituted arylsulfonyl, carboxy, carbamoyl, substituted carbamoyl, cycloalkyl, substituted cycloalkyl, cycloheteroalkyl, substituted cycloheteroalkyl, dialkylamino, substituted dialkylamino, heteroaryloxy, substituted heteroaryloxy, heteroaryl, substituted heteroaryl, heteroalkyl, and substituted heteroalkyl;

$R_3$ is a member independently selected from the group consisting of alkyl, substituted alkyl, acyl, substituted acyl, acylamino, substituted acylamino, alkylamino, substituted alkylamino, alkoxycarbonyl, substituted alkoxycarbonyl, alkylarylamino, substituted alkylarylamino, aryl, substituted aryl, arylalkyl, substituted arylalkyl, arylamino, substituted arylamino, carbamoyl, substituted carbamoyl, dialkylamino, substituted dialkylamino, heteroaryl, substituted heteroaryl, heteroalkyl, and substituted heteroalkyl;

each $R_5$ is a member independently selected from the group consisting of alkyl, acyl, substituted acyl, acylamino, substituted acylamino, alkylamino, substituted alkylamino, alkylarylamino, substituted alkylarylamino, amino, aryl, substituted aryl, arylalkyl, substituted arylalkyl, arylsulfonyl, substituted arylsulfonyl, azido, carboxy, carbamoyl, substituted carbamoyl, carboxyl, cyano, cycloalkyl, substituted cycloalkyl, cycloheteroalkyl, substituted cycloheteroalkyl, dialkylamino, substituted dialkylamino, halo, heteroaryl, substituted heteroaryl, hydroxyl, and nitro; and one or more drugs useful in treating cardiovascular diseases, vasoconstriction or vascular occlusive disorders.

29. The method of claim 1 or 2, wherein the modulator has a formula selected from:

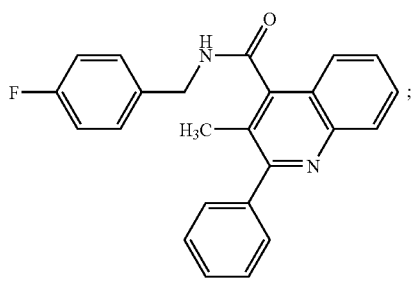

101

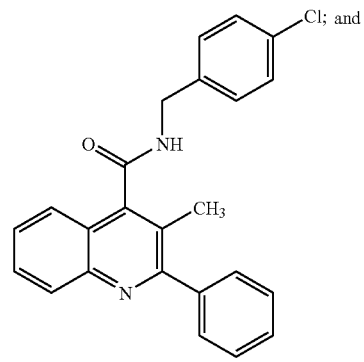

105

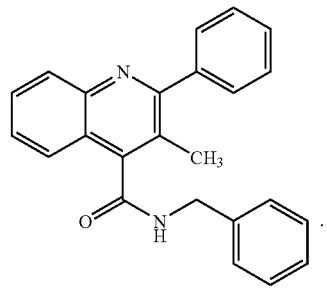

107

30. A method of treating a disease in a patient comprising: administering to the patient a therapeutically effective amount of a modulator of an Edg-3 receptor wherein the modulator is a compound of Formula (VIa):

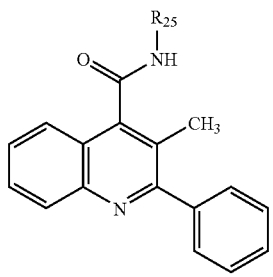

(VIa)

or a pharmaceutically acceptable solvate or hydrate thereof, wherein $R_{25}$ is a benzyl, group, and wherein said disease is a member selected from cardiovascular disease, ischemia, atherosclerosis, vasoconstriction and vascular occlusive disorder.

31. The method according to claim 30, wherein said $R_{25}$ is an unsubstituted benzyl group.

32. The method according to claim 30, wherein said $R_{25}$ is a substituted benzyl group.

33. The method according to claim 32, wherein said substituted benzyl group is

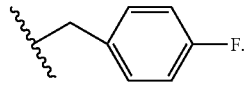

34. The method according to claim 32, wherein said substituted benzyl group is

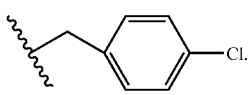

* * * * *